(12) United States Patent
Song et al.

(10) Patent No.: US 9,989,474 B2
(45) Date of Patent: Jun. 5, 2018

(54) GAS SENSOR, REFRIGERATOR HAVING THE SAME, AND METHOD FOR MANUFACTURING THE GAS SENSOR

(71) Applicants: Samsung Electronics Co., Ltd., Suwon-si (KR); SENKO CO., LTD., Osan-si (KR)

(72) Inventors: Youn Joo Song, Suwon-si (KR); Seung Chul Ha, Suwon-si (KR); Hyun Joo Jung, Seoul (KR); Young Chul Ko, Suwon-si (KR); Yong Won Jeong, Seoul (KR)

(73) Assignees: SAMSUNG ELECTRONICS CO., LTD., Suwon-si (KR); SENKO CO., LTD., Osan-si (KR)

( * ) Notice: Subject to any disclaimer, the term of this patent is extended or adjusted under 35 U.S.C. 154(b) by 35 days.

(21) Appl. No.: 14/721,203

(22) Filed: May 26, 2015

(65) Prior Publication Data

US 2016/0018338 A1 Jan. 21, 2016

(30) Foreign Application Priority Data

Jul. 21, 2014 (KR) ........................ 10-2014-0092023

(51) Int. Cl.
*G01N 21/75* (2006.01)
*G01N 21/78* (2006.01)
*G01N 31/22* (2006.01)

(52) U.S. Cl.
CPC ......... *G01N 21/783* (2013.01); *G01N 31/221* (2013.01)

(58) Field of Classification Search
CPC ........................... G01N 21/783; G01N 31/221
See application file for complete search history.

(56) References Cited

U.S. PATENT DOCUMENTS 3,067,015 A * 12/1962 Lawdermilt .................. 116/206
6,428,748 B1 * 8/2002 Wallach ................. G01N 21/78
422/421

(Continued)

FOREIGN PATENT DOCUMENTS

EP 0342783 11/1989
EP 1609488 12/2005

(Continued)

OTHER PUBLICATIONS

Extended European Search Report dated Dec. 15, 2015 in European Patent Application No. 15168711.8.

(Continued)

*Primary Examiner* — Dennis White
(74) *Attorney, Agent, or Firm* — Staas & Halsey LLP

(57) ABSTRACT

A gas sensor, a refrigerator having the gas sensor, and a method for controlling the gas sensor recognizes the ripening degree of a target food on the basis of a variation in color using a pH indicator having a color that is changed with pH variation generated when the pH indicator reacts with target gas, a refrigerator having the gas sensor. The gas sensor for detecting target gas includes: a base provided for gas permeation; and a detection unit provided at the base, and is discolored in response to pH variation generated when reacting with target gas having permeated the base.

25 Claims, 36 Drawing Sheets

(56) References Cited

U.S. PATENT DOCUMENTS

| | | | |
|---|---|---|---|
| 2003/0143112 A1* | 7/2003 | Suslick | G01N 21/272 422/400 |
| 2006/0057022 A1 | 3/2006 | Williams et al. | |
| 2009/0010804 A1* | 1/2009 | Withrow, III | A61B 5/0002 422/68.1 |
| 2012/0107191 A1 | 5/2012 | Strahle et al. | |

FOREIGN PATENT DOCUMENTS

| | | | | |
|---|---|---|---|---|
| KR | 10-1997-0007229 | | 2/1997 | |
| WO | 96/24054 | | 8/1996 | |
| WO | WO 2005047788 A1 * | 5/2005 | | F25D 17/042 |
| WO | 2008/079024 | | 7/2008 | |
| WO | WO 2008079024 A1 * | 7/2008 | | G01N 21/783 |

OTHER PUBLICATIONS

European Office Action dated Dec. 19, 2017 in European Patent Application No. 15168711.8.

Byoung-Yong Chang, "Smartphone-based Chemistry Instrumentation: Digitization of Colorimetric Measurements", *Bull. Korean Chem. Soc.*, 2012, vol. 33, No. 2, 4 pages.

* cited by examiner

FIG. 9

| MOLEC | CO2 | O2 | ALCOHOL | ACETIC ACID | H2 | N2 | ALDEHYDE (Acetaldehyde) | SULFUR COMPOUND (Methylmer captene) |
|---|---|---|---|---|---|---|---|---|
| H-CONST | 0.03 | 0.001 | 100 | ACETIC ACID | 0.0007 | 0.0006 | 10 | 0.3 |
| FEATURES | NON-POLARITY | NON-POLARITY | POLARITY | POLARITY | NON-POLARITY | NON-POLARITY | POLARITY | NON-POLARITY |

GAS SENSOR, REFRIGERATOR HAVING THE SAME, AND METHOD FOR MANUFACTURING THE GAS SENSOR

CROSS-REFERENCE TO RELATED APPLICATIONS

This application claims the priority benefit of Korean Patent Application No. 10-2014-0092023, filed on Jul. 21, 2014 in the Korean Intellectual Property Office, the disclosure of which is incorporated herein by reference.

BACKGROUND

1. Field

The following description relates to a gas sensor for measuring the amount of target gas, an electronic product having the gas sensor, and a method for manufacturing the gas sensor.

2. Description of the Related Art

A gas sensor measures the density of specific gas, and is classified into a semiconductor gas sensor, a contact combustion gas sensor, and an electrochemical gas sensor, etc. From among the above-mentioned gas sensors, the semiconductor gas sensor measures the influence of resistance changed when a target material to be measured is oxidized or reduced, and the electrochemical gas sensor measures the amount of ions generated by oxidizing/reducing gas dissolved in electrolyte so that it can measure the density of gas.

Because most gas other than inert gas has a tendency of oxidation-reduction, the semiconductor gas sensor and the electrochemical gas sensor unavoidably generate crosstalk in which the target gas to be measured and other gases are simultaneously measured. Therefore, there is a limitation in measurement selectivity through which a specific gas can be selectively measured.

In addition, whereas the olfactory organ of a human being can sense a ppb-level gas emitting a smell, the measurement sensitivity of a conventional gas sensor is less than that of the human olfactory organ. The conventional gas sensor has difficulty in measuring gas of a ppm level or lower.

SUMMARY

Therefore, it is an aspect of the disclosure to provide a gas sensor configured to recognize the ripening degree of a target food on the basis of a variation in color using a pH indicator having a color that is changed with pH variation generated when the pH indicator reacts with target gas, a refrigerator having the gas sensor, and a method for controlling the gas sensor.

It is an aspect of the disclosure to provide a refrigerator configured to decide a state of target food by sensing a color change of a gas sensor, recognize a position of a storage chamber including rotten target food, and a method for controlling the gas sensor.

Additional aspects of the disclosure will be set forth in part in the description which follows and, in part, will be obvious from the description, or may be learned by practice of the disclosure.

In accordance with an aspect of the disclosure, a gas sensor for detecting target gas includes: a base provided for gas permeation; and a detection unit provided at the base, and discolored in response to pH variation generated when reacting with target gas having permeated the base.

The detection unit may include a hydrophilic membrane having a detection solution.

The detection solution may include at least one pH indicator that is discolored in response to pH variation generated when the detection solution reacts with the target gas.

If acetic acid is contained in the target gas, the detection solution may include at least one pH indicator from among a bromothymol blue pH indicator from approximately 0.001 weight percent to approximately 0.1 weight percent and a chlorophenol red pH indicator from approximately 0.001 weight percent to approximately 0.1 weight percent.

The detection solution may include a buffer solution having a dissociation constant (pKa) of 3 to 10.

The buffer solution may include at least one of sodium acetate, sodium carbonate, sodium bicarbonate, and sodium citrate.

The sodium acetate buffer solution may include acetate ions of approximately 0.1 mM to approximately 1000 mM.

The detection solution may include a buffer solution in which conjugate ions having the same dissociation constant as in the target gas are dissolved.

The resolution of the gas sensor may be changed according to density of conjugate ions dissolved in the buffer solution.

If the target gas is volatile organic acid, the detection solution may include a buffer solution having an initial pH value higher than a dissociation constant of target gas.

The sensing range of the target gas may be changed according to the initial pH value of the buffer solution.

The detection solution may include at least one of glycerin, ethylene glycol, polyethylene glycol, and calcium chloride.

The detection solution may be absorbed in the hydrophilic membrane and fixed thereto.

The hydrophilic membrane may include at least one of cellulose ester, glass fiber, cellulose acetate, cellulose fiber, litmus paper, Korean traditional paper, and filter paper.

The base may include a hydrophobic membrane needed for gas permeation.

The base may include at least one of polytetrafluoroethylene, thermoplastic polyurethane, polyethylene, low density polyethylene, linear low density polyethylene, high density polyethylene, and Tyvek.

The gas sensor may further include: a transparent membrane attached to the detection unit, and configured to prevent gas permeation.

The target gas may include gas generated from a ripening process of food.

The gas sensor may further include: an image detection unit configured to obtain an image of the detection unit; and a transmitter configured to output data regarding an image detected from the image detection unit to an external part.

The gas sensor may further include: a battery configured to provide a power source to the image detection unit and the transmitter.

The gas sensor may further include: a wireless power receiving unit configured to provide a power source to the image detection unit and the transmitter.

In accordance with an aspect of the disclosure, a refrigerator includes: a gas sensor including a base provided for gas permeation and a detection unit provided at the base, the detection unit being discolored in response to pH variation generated when reacting with target gas having permeated the base; and an image sensor configured to obtain an image of the gas sensor.

The refrigerator may further include: a controller configured to determine a state of target food and a storage position of the target food on the basis of the gas sensor image obtained from the image sensor.

The controller may be configured to pre-store data regarding discoloration of the gas sensor and the target food state based on the discoloration.

The controller may determine a color difference between one color obtained before exposure to target gas and another color obtained after exposure to the target gas using the image obtained from the image sensor, and determine a state of the target food on the basis of the determined color difference using the pre-stored data.

The refrigerator may further include: a display unit configured to display the target food state decided on the basis of the gas sensor image obtained from the image sensor or to display information regarding a storage position of the target food.

In accordance with an aspect of the disclosure, a method for manufacturing a gas sensor includes: fixing a detection solution to a hydrophilic membrane; and attaching the hydrophilic membrane to a hydrophobic membrane through which gas permeates.

The fixing of the detection solution to the hydrophilic membrane may include: absorbing the detection solution, which includes a pH indictor, a buffer solution, a moisture absorbent, into the hydrophilic membrane; and heating the hydrophilic membrane in which the detection solution is absorbed at a predetermined temperature for a predetermined time.

The method may further include: heat-bonding a transparent membrane for preventing gas permeation to the hydrophilic membrane attached to the hydrophobic membrane.

BRIEF DESCRIPTION OF THE DRAWINGS

These and/or other aspects of the disclosure will become apparent and more readily appreciated from the following description of the embodiments, taken in conjunction with the accompanying drawings of which:

FIG. 9 is a diagram illustrating characteristics of gas types generated in kimchi fermentation and Henry constants.

DETAILED DESCRIPTION

Figure 1:
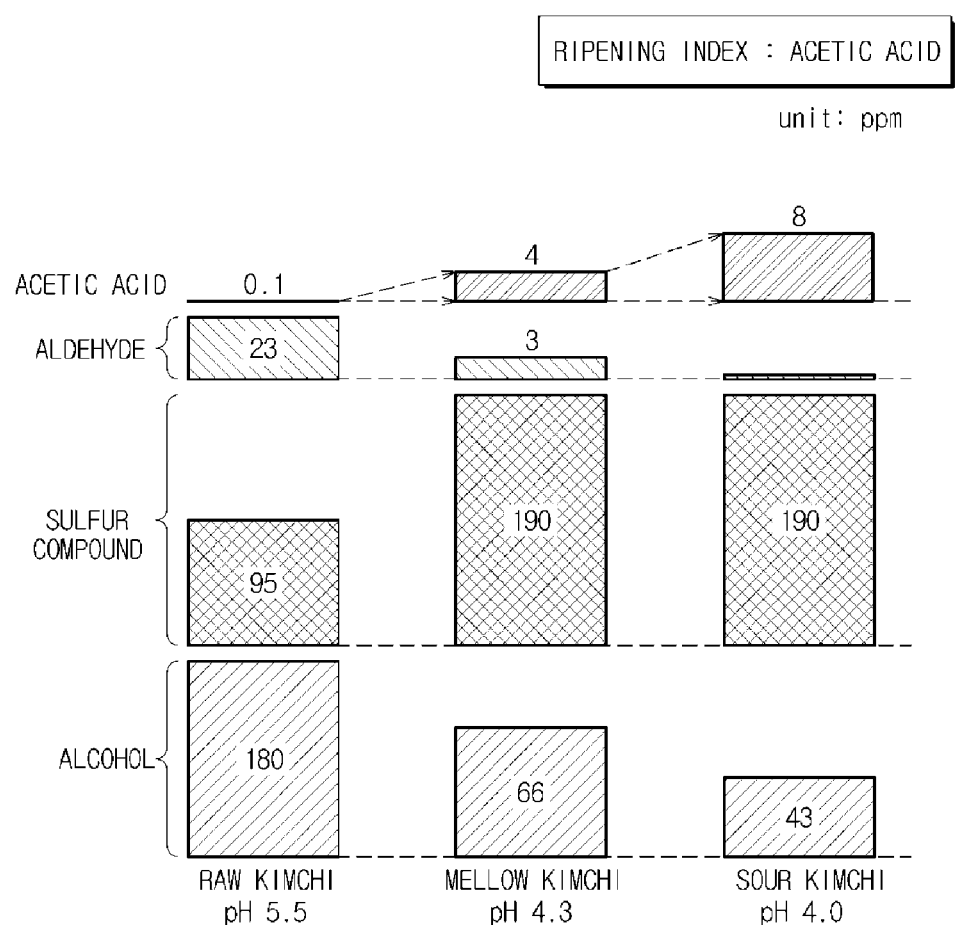
FIG. 1 is a diagram illustrating categories and density of gas generated in response to the ripening degree of kimchi.

Reference will now be made in detail to the embodiments of the disclosure, examples of which are illustrated in the accompanying drawings, wherein like reference numerals refer to like elements throughout.

A gas sensor, a refrigerator having the gas sensor, and a method for manufacturing the gas sensor according to embodiments of the disclosure will hereinafter be described with reference to the attached drawings.

A gas sensor according to embodiments of the disclosure can be used in various technical fields that measure specific gases. For example, the various technical fields may include environment management fields, safety management fields, medical diagnosis fields, food management fields, etc. For detailed description of structures and operations of the devices according to the disclosure, the following embodiment will disclose the exemplary case in which the gas sensor is used in food management monitoring a state of food.

FIG. 1 is a diagram illustrating categories and density of gas generated in response to the ripening degree of kimchi. However, the disclosure is not limited to detecting a degree of ripening of kimchi, such that detection of an emitted gas from any food may be performed.

Various kinds of gas may be generated in the ripening or rotting time of food. The category and amount of generated gas are affected by the ripening degree of food, added spices or added materials, etc.

Gas components closely related to the ripening degree of food from among the generated gas may include volatile organic acid, ammonia, etc. The gas components are not detected in a fresh state of food, and the density of gas components increases in proportion to the ripening degree of food.

Referring to FIG. 1, if a fermented food (such as kimchi, for example) ripens, various gases, for example, acetic acid, aldehydes, sulfur compounds, alcohols, etc., may be generated. Although the principal gas generated in the ripening process of kimchi may be aldehydes, sulfur compounds, alcohol, etc., the principal gas is gas based on foodstuffs such as salted seafood, spices, etc. so that the principal gas may not be absolutely associated with fermentation of kimchi or the ripening degree of kimchi.

Gas directly affecting fermentation is a volatile organic acid generated as a by-product of microbes. As can be seen from the example of FIG. 1, the volatile organic acid indicates acetic acid. As can be seen from FIG. 1, little acetic acid is generated in an initial fermentation process, and is then gradually increased in response to the progress of fermentation. Therefore, the acetic acid may be used as an index for deciding the ripening degree of kimchi. However, the density of acetic acid is much lower than that of other gas. For example, acetic acid may have a density of approximately a few ppm.

Therefore, in order to recognize the ripening degree of fermented food such as kimchi, it is necessary to detect volatile organic acid having density of 1 ppm or less, from among other gases having a density corresponding to a maximum of several hundred ppm.

The olfactory organ of most people can discriminate volatile organic acid from other gases even at a selectivity of one-to-several hundred, and there is a little difference in selectivity among people. However, most commercially available gas sensors may have difficulty in selectively measuring only the volatile organic acid having density of approximately several ppm from among other gas components having density of several hundred ppm.

Figure 2:
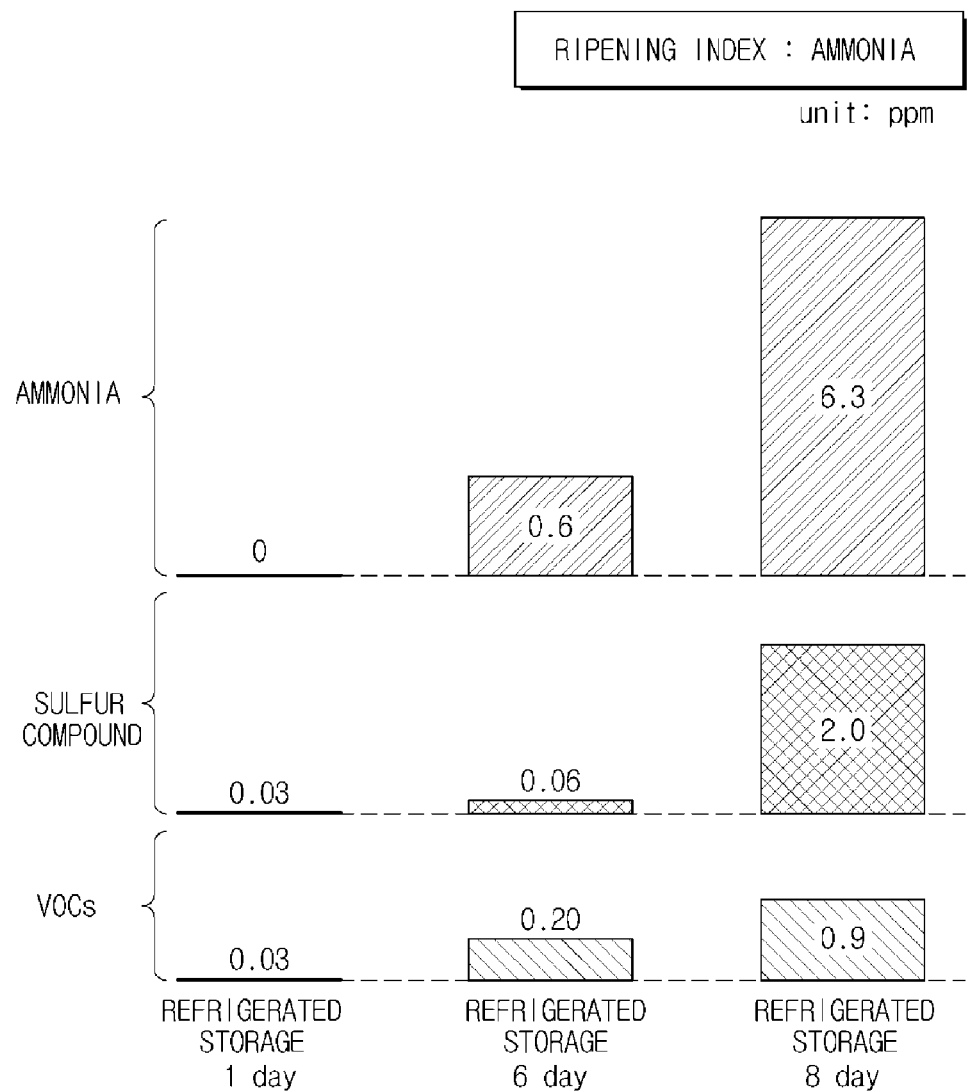
FIG. 2 is a diagram illustrating categories and density of gas generated in response to the ripening degree of meat.

In the case of general food but not the fermented food, the ripening or rotten degree of the general food can be derived from gas components generated in the general food. If meat is stored at a low temperature for a long time, protein is decomposed by microbes, so that amino acid is increased. The ripening process of such meat may be basically considered a gradual rotting process. Referring to FIG. 2, during the ripening process of meat, various gases, for example, ammonia, sulfur compounds, aldehydes, Volatile Organic Compounds (VOCs), may occur in an amino-acid metabolic process caused by germs propagated in protein. Gases, such as sulfur compounds, aldehydes, VOCs, etc. may be modified according to categories or parts of meat within the same kind of gas. Therefore, ammonia may be used as gas that can be used as an index for indicating the ripening or rotten degree of meat.

FIG. 2 is a diagram illustrating categories and density of gas generated in response to the ripening degree of meat.

Referring to FIG. 2, although a foodstuff is stored in a refrigerating chamber for several days (for example, 6 days), a very small amount of ammonia gas occurs so that a human being has difficulty in smelling the ammonia gas. A small amount of ammonia gas occurs in response to the ripening degree of meat, so that a resolution of 1 ppm or less is needed to correctly recognize the ripening degree of the corresponding meat. The resolution and sensitivity may be factors indicating a minimum density capable of being measured by sensors.

As described above, in order to recognize the fermentation degree or the ripening degree of food, high selectivity and high sensitivity (resolution of sub ppm) are needed so that specific gas of a ppm level from among plural gases having density of several hundreds of ppm can be selectively detected.

The gas sensor according to an embodiment of the disclosure can be implemented to have high selectivity and high sensitivity (resolution of sub ppm) using principles similar to that of the olfactory system of a human being, and the structure and operation principles of the gas sensor according to an embodiment of the disclosure will hereinafter be described in detail.

Figure 3:
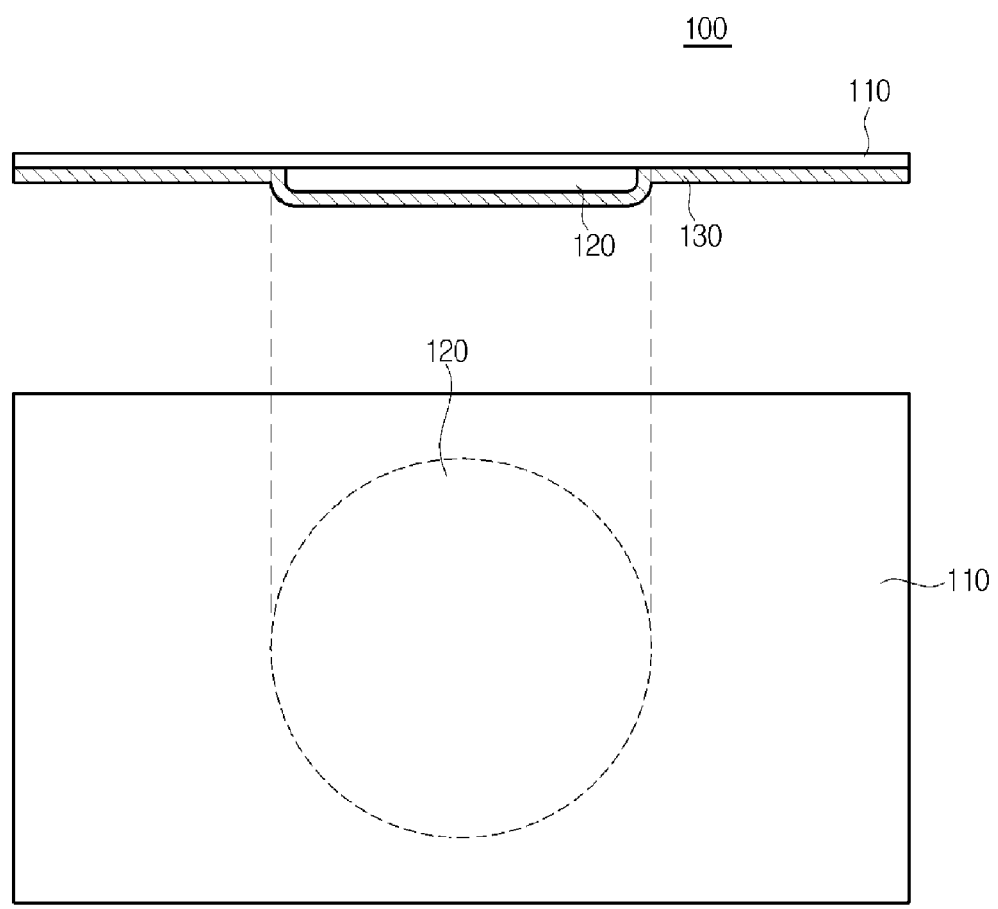
FIGS. 3, 4, and 5 are diagrams illustrating a gas sensor according to an embodiment of the disclosure.
Figure 4:
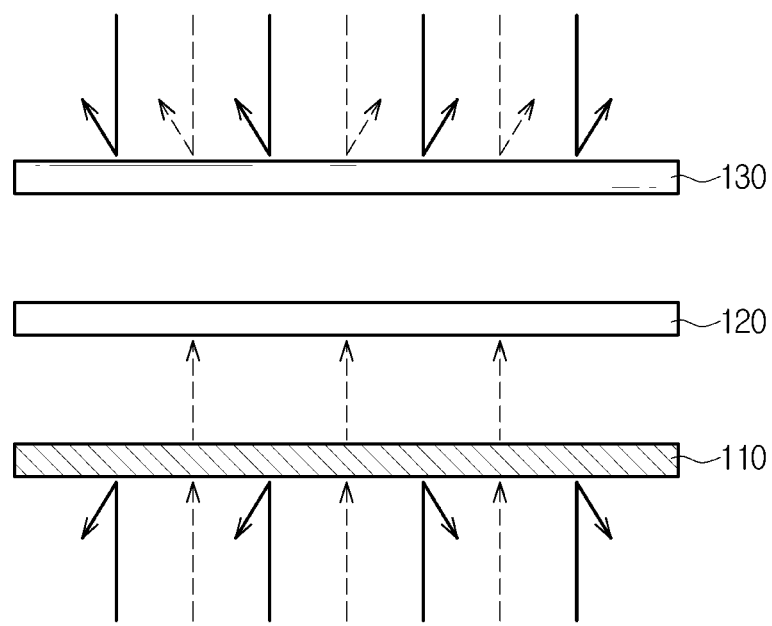
Figure 5:
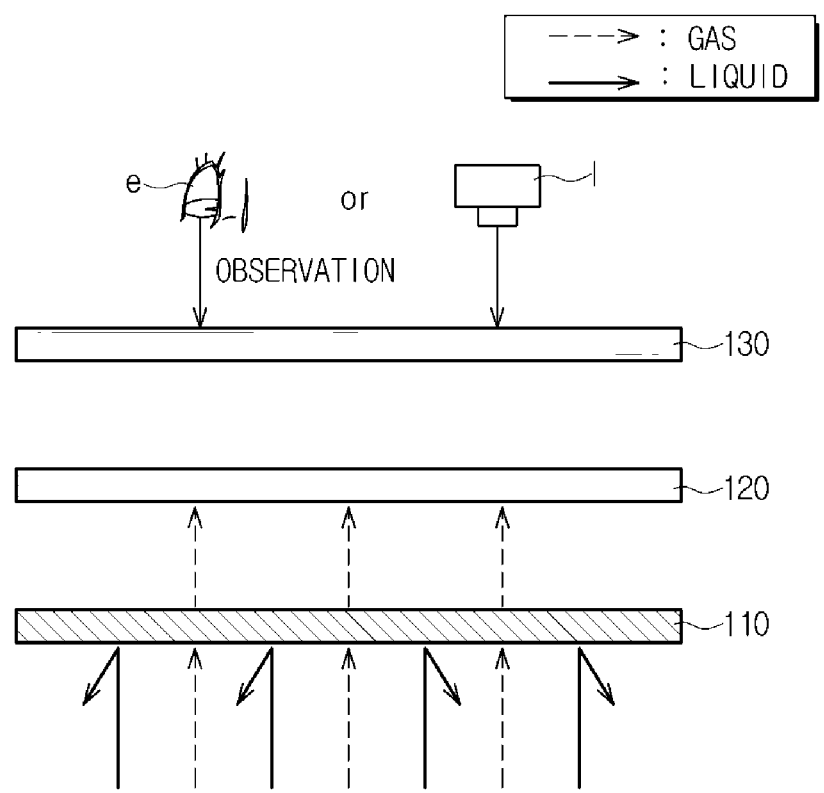

FIGS. 3 to 5 are diagrams illustrating a gas sensor according to an embodiment of the disclosure.

Referring to FIG. 3, the gas sensor 100 according to an embodiment may include a base 110, a detection unit, or detector, 120 provided on the base 110, and a transparent membrane 130 attached to the detection unit 120 to cover the detection unit 120. Target gas reacts with the detection unit 120 after passing through the base 110. The detection unit 120 is discolored in response to pH variation generated upon reaction with the target gas. That is, the detection unit 120 may determine whether or not the target gas is detected on the basis of a color change.

The base 110 may be implemented as a hydrophobic membrane. For example, most hydrophobic gas permeability materials may be used as the base 110. For example, polytetrafluoroethylene, thermoplastic polyurethane, polyethylene, low density polyethylene, linear low density polyethylene, high density polyethylene, Tyvek, etc. may be used as the base 110.

The detection unit 120 may detect gas generated in foodstuff by reacting with the gas, the base 110 formed of the above-mentioned materials may prevent permeation of liquid to prevent a liquid material from reacting with the detection unit 120. That is, as can be seen from FIG. 4, whereas gas being shifted to the base 110 arrives at the detection unit 120 after passing through the base 110, liquid shifted to the base 110 does not pass through the base 110 so that the liquid does not arrive at the detection unit 120. A transparent membrane 130 may be formed of a gas non-permeable material in such a manner that gas having passed through the base 110 can arrive at the detection unit 120. That is, as can be seen from FIG. 4, the transparent membrane 130 may prevent permeation of gas and liquid.

The transparent membrane 130 may be attached to the detection unit 120 to cover the detection unit 120 attached to the base 110. As can be seen from FIG. 5, a color change of the detection unit 120 can be observed through the transparent membrane 130. A user (e) can immediately view color change of the detection unit 120 through the transparent membrane 130. Alternatively, the image sensor (I) may obtain an image of color change of the detection unit 120 through the transparent membrane 130. When the gas sensor 100 is mounted to a predetermined container storing foodstuffs therein, the base 110 and the foodstuff may face each other, and the transparent membrane 130 may be attached to the container.

Figure 6:
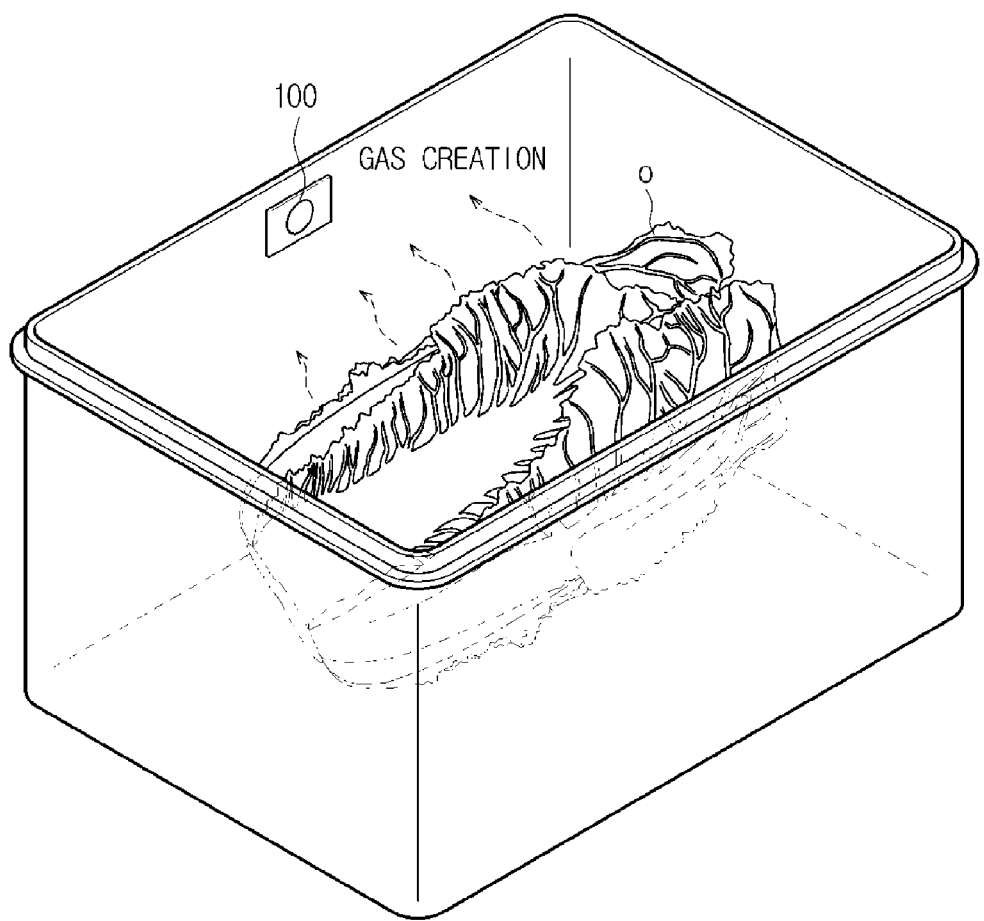
FIGS. 6, 7, and 8 are conceptual diagrams illustrating the appearance of the gas sensor mounted to a container according to an embodiment of the disclosure.
Figure 7:
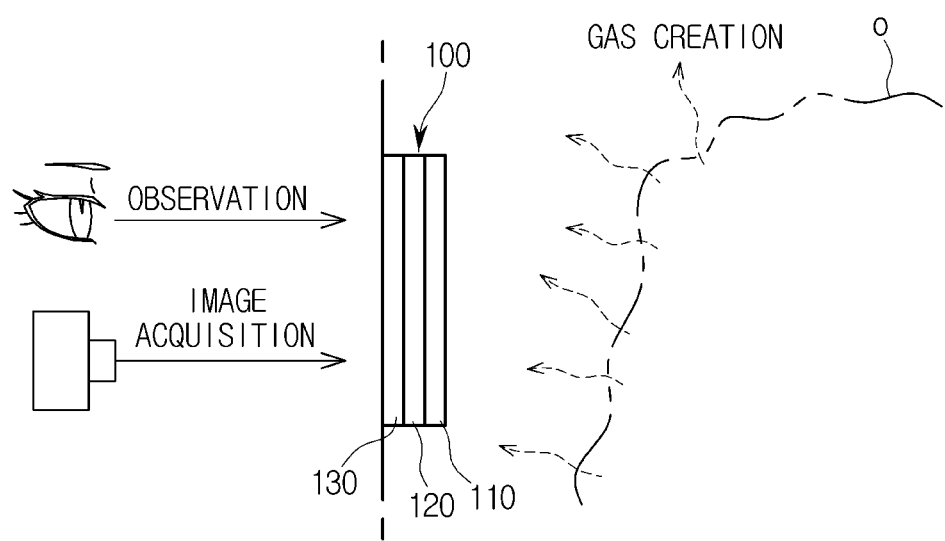
Figure 8:
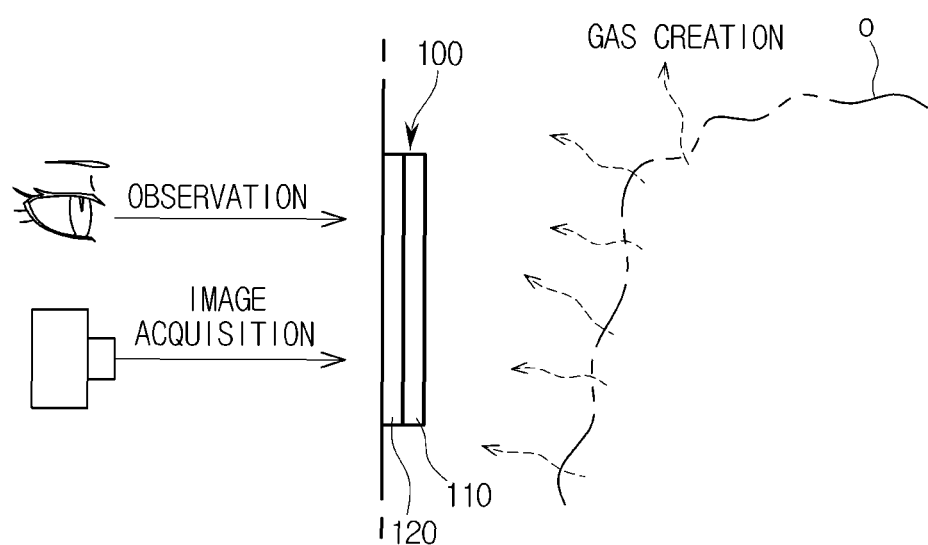

FIGS. 6 to 8 are conceptual diagrams illustrating the appearance of the gas sensor mounted to a container according to an embodiment of the disclosure.

Referring to FIGS. 6 and 7, when the gas sensor 100 is mounted to a predetermined container, the base 110 is installed to face a target food (O) accommodated in the container. Gas generated from the target food (O) arrives at the detection unit 120 after passing through the base 110. Because the base 110 is located to face the target food (O) present in the container, color change of the detection unit 120 is observed from a back surface of the base 110. Therefore, the transparent membrane 130 formed of transparent resin through which the user can observe color change of the detection unit 120 is installed to cover the detection unit 120. The user can directly observe color change of the gas sensor 100 through the transparent membrane 130, and the image sensor may detect the color change of the gas sensor 100 through the transparent membrane 130. A detailed description thereof will be given later.

Assuming that a specific part to which the gas sensor 100 is attached is formed of a transparent material, the user can immediately observe color change of the gas sensor 100. If the gas sensor 100 is mounted to a part formed of an opaque material, it is impossible for the user to observe color change of the gas sensor 100. A method for mounting the gas sensor 100 to the part formed of an opaque material that enables the user to observe color change of the gas sensor 100 will hereinafter be described in detail.

If the gas sensor 100 is attached to a predetermined container, the transparent membrane 130 may be omitted and the detection unit 120 may be immediately attached to the container as can be seen from FIG. 8. That is, because the container can serve as the transparent membrane 130, the transparent membrane 130 may be omitted. In this case, it may be preferable that the gas sensor 100 be attached to a transparent part of the container.

The detection unit 120 may be implemented as a hydrophilic membrane having a detection solution. The hydrophilic membrane may be implemented as hydrophilic materials including cellulose ester, glass fiber, cellulose acetate, cellulose fiber, litmus paper, traditional Korean paper, filter paper, etc. The detection solution discolored by reacting with the target gas may be absorbed into the hydrophilic membrane, so that the detection solution is then fixed.

As described above, the gas sensor is designed to use the principles of the human olfactory system, and the detection unit fixed by absorption of the detection solution can function as a mucus layer of human epithelium tissues that collect scent molecules from air.

When determining the fermentation degree or the ripening degree of foodstuff, especially, when determining the ripening degree of kimchi, the volatile organic acid gas such as acetic acid may be used as an important index. Therefore, the gas sensor may use the volatile organic acid gas as the target gas. That is, the gas sensor may be configured to measure the density of volatile organic acid gas.

The volatile organic acid gas is dissolved only in a polar solvent such as water, and may selectively capture water-soluble molecules such as volatile organic acid, other than fat-soluble molecules such as sulfur compounds or VOCs, from among a plurality of gas components present in the external environment of the gas sensor. That is, the detection solution may serve to filter most sulfur compounds and VOCs generated in foodstuffs, so that selectivity of target gas of the gas sensor is improved.

FIG. 9 is a diagram illustrating characteristics of gas types generated in kimchi fermentation and Henry constants.

Gaseous molecules may have different dissolving degrees according to categories of gas. The Henry constant may be used as an index indicating that gaseous molecules are converted into a liquid state so that the Henry constant can represent the degree of gas dissolution. The Henry constant is proportional to the amount of water-soluble characteristics. The lower the Henry constant, the higher the amount of water non-soluble characteristics.

Referring to FIG. 9, polar gas from among plural gases generated during the kimchi fermentation may include alcohols, aldehydes, and acetic acid, and the remaining gases other than the polar gas may be carbon dioxide ($CO_2$), oxygen ($O_2$), alcohols, aldehydes, hydrogen ($H_2$), and nitrogen ($N_2$), each of which is non-polar. The carbon dioxide ($CO_2$), oxygen ($O_2$), alcohol, aldehyde, hydrogen ($H_2$), and nitrogen ($N_2$) having non-polarity do not dissolve easily in the detection solution.

Gas having the highest Henry constant is acetic acid acting as the volatile organic acid. Here, the Henry constant ranges from 5000 to 10000, and is hundreds of times to millions of times larger than those of the remaining gases. This means that acetic acid can be hundreds of times to millions of times more easily dissolved in water than other gases.

The Henry constant of the acetic acid is higher than those of $CO_2$, $O_2$, $H_2$, $N_2$, sulfur compound, and is also higher than those of alcohols and aldehydes. The gas sensor including the detection solution can capture the acetic acid from among various fermentation gases generated from kimchi with very high selectivity.

The acetic acid from among various gases generated in the fermentation process of kimchi most highly influences the pH of an aqueous solution. Therefore, the gas sensor can measure the density of acetic acid with superior resolution. Although a very small amount of alcohols, aldehydes, or sulfur compounds can be dissolved in the aqueous solution, the alcohols, aldehydes, or sulfur compounds have little effect on a pH of the aqueous solution, so that selectivity of the gas sensor can be secondarily enhanced.

When volatile organic acid is dissolved in the detection solution, the volatile organic acid is dissociated, so that the density of $H_2$ ions is unexpectedly changed. Acetic acid acting as a representative volatile organic acid is used as target gas, and a method for designing the detection solution through which the gas sensor may have superior selectivity and resolution will hereinafter be described in detail.

The detection solution may include a buffer solution, a pH indicator, and a moisture absorbent. The buffer solution can adjust the reaction sensitivity of the volatile organic acid and the sensing range of the volatile organic acid. The pH indicator indicates pH variation generated when the volatile organic acid reacts with the detection solution. The moisture absorbent can suppress moisture evaporation.

If acetic acid is dissolved in the detection solution, the acetic acid is dissociated into acetate ions and $H_2$ ions as denoted by the following chemical formula 1. This operation will be referred to as dissociation.

$$CH_3COOH \leftrightarrow CH_3COO^- + H^+ \qquad \text{[Chemical formula 1]}$$

The degree of dissociation of the acetic acid from the detection solution may be represented by an ionization constant or a Henry constant according to the following equation 1.

$$K_a = [CH_3COO^-][H^+]/[CH_3COOH] = 1.8 \times 10^{-5} \qquad \text{[Equation 1]}$$

That is, the ionization constant (Ka) of the acetic acid, denoted by $1.8 \times 10^{-5}$ is considered a very low value, so that the ionization constant (Ka) may also be denoted by pKa 4.7.

After the acetic acid has been dissociated, unique characteristics of the original acetic acid are lost, and pH is gradually reduced in response to successive dissociation.

Figure 10:
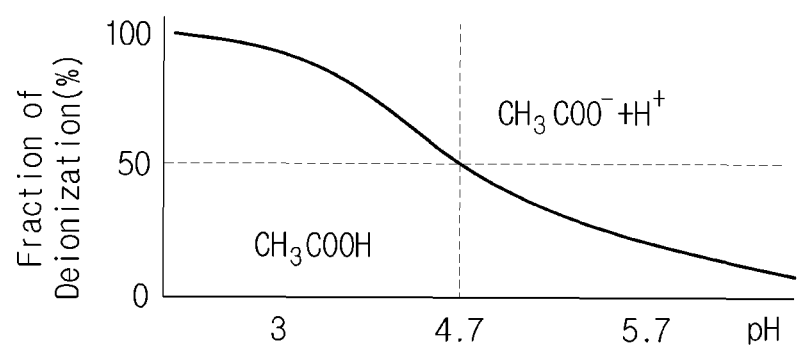
FIG. 10 is a graph illustrating a dissociation curve of acetic acid in response to pH variation of a detection solution.

FIG. 10 is a graph illustrating a dissociation curve of acetic acid in response to pH variation of a detection solution.

As can be seen from the graph of FIG. 10, the Y-axis may denote a fraction of deionization. The fraction of deionization is proportional to the dissociation.

Referring to FIG. 10, assuming that a pH of the detection solution in which acetic acid is dissolved is identical to pKa (i.e., 4.7) of the acetic acid, the acetic acid has a dissociation of approximately 50%, a half of the acetic acid is dissociated so that unique characteristics of the acetic acid are lost, and the remaining half of the acetic acid is not dissociated, so that characteristics of the acetic acid can be maintained.

Assuming that a pH of the detection solution is lower than 4.7, the dissociation of the acetic acid is rapidly decreased, so that most of acetic acid is not dissociated and can be maintained without change.

In contrast, assuming that a pH of the detection solution is higher than 4.7, the dissociation of the acetic acid is increased, so that the acetic acid can be successively dissociated. If the acetic acid is successively dissociated in the detection solution, H2 ions of the detection solution are increased, resulting in pH reduction. If the pH value of the detection solution is reduced, the acetic acid having a predetermined density or higher is not dissociated and remains. If the acetic acid acting as the volatile organic acid is not dissociated and is present in the detection solution, the acetic acid may be re-evaporated.

Therefore, if the detection solution is exposed to the environment in which the acetic acid having a predetermined density is present, the acetic acid dissolved in the detection solution is successively dissociated, and a pH value is reduced and the non-dissociated acetic acid is evaporated, so that gas received from the external part and the evaporated gas reach a dynamic equilibrium state. That is, an equilibrium state in which a pH of the detection solution remains unchanged is achieved.

In addition, if the acetic acid is not present in the external environment, the acetic acid contained in the detection solution is successively evaporated, so that the pH value is increased again. The gas sensor can guarantee reversible characteristics using the above-mentioned principles, and can adjust the sensing resolution and the sensing range.

The gas sensor may have different sensing ranges and different sensing ranges according to its own usages, where a composition ratio of the detection solution and the buffer solution is adjusted so that a desired sensing range and a desired sensing resolution can be achieved.

The following equation 2 may indicate the Henderson-Hasselbalch equation between the acetic acid derived from Equation 1 and the acetate ion. In this case, the acetic acid and the acetate ion have the relationship of conjugate acid-conjugate base.

$$pH = pK_a + \log [CHCOO^-]/[CH_3COOH]N \quad \text{[Equation 2]}$$

Referring to Equation 2, a pH of the detection solution is determined by the ratio of the acetate ion to the acetic acid. Therefore, if the acetate ions are previously dissolved in the initial detection solution, a pH reactivity of the acetate acid is changed according to the amount of dissolved acetate ions.

Therefore, the amount of acetate ions dissolved in the initial buffer solution and the initial pH value of the buffer solution are adjusted, so that the reactivity and the sensing range of the target gas to be measured can be adjusted.

Figure 11:
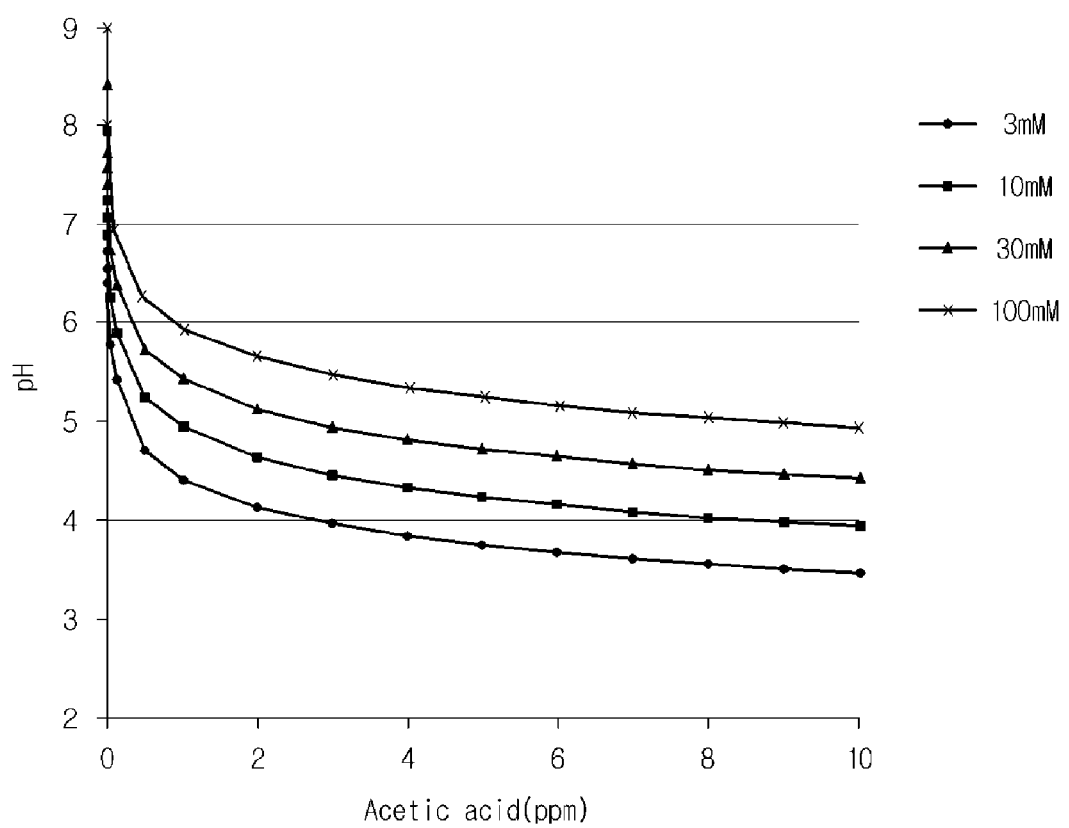
FIG. 11 is a graph illustrating that pH variation of a buffer solution in response to the density of acetic acid of the external environment is generated in response to the amount of acetate ions dissolved in the buffer solution.
Figure 12:
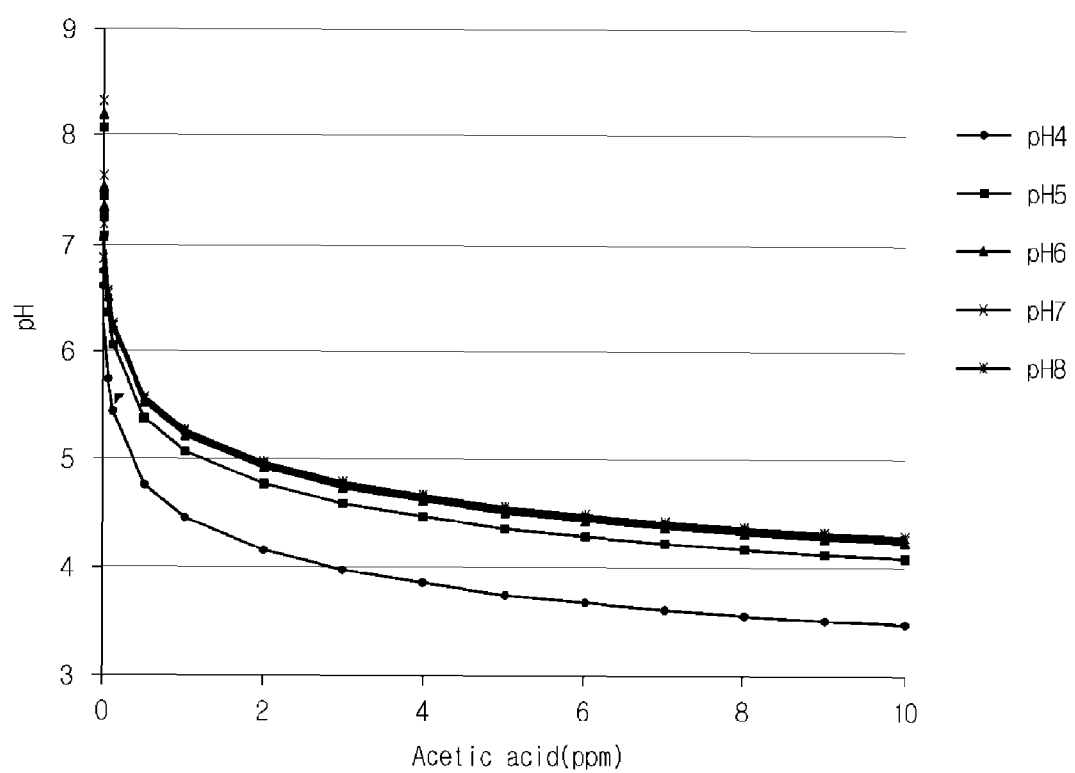
FIG. 12 is a graph illustrating that pH variation of a buffer solution in response to the density of acetic acid of the external environment is generated in an initial pH of the buffer solution.

FIG. 11 is a graph illustrating that pH variation of a buffer solution in response to the density of acetic acid of the external environment is generated in response to the amount of acetate ions dissolved in the buffer solution. FIG. 12 is a graph illustrating that pH variation of a buffer solution in response to the density of acetic acid of the external environment is generated in an initial pH of the buffer solution.

The graph of FIG. 11 shows that pH variation in response to the density of acetic acid gas of the buffer solution having an initial pH of 8 is calculated at each ion density (3 mM, 10 mM, 30 mM, 100 mM). The density of initial acetate ion may indicate the density of acetate ions dissolved in the buffer solution.

Referring to FIG. 11, if the initial acetate ion is set to 3 mM, the highest pH variation of the buffer solution occurs in response to density variation of acetic acid gas. Especially, a high pH variation also occurs in the acetic acid gas of 1 ppm or less. Therefore, it can be recognized that reactivity with the acetic acid gas has superior reactivity as the density of initial acetate ions is gradually reduced.

Meanwhile, although the subacid acetic acid has a higher density, it is substantially difficult to drop a pH value of the buffer solution down to 3 or less. As a result, assuming that the initial acetate ion has the density of 3 mM, it may be difficult to measure the density of acetic acid gas of 10 ppm or higher.

On the contrary, assuming that the initial acetate ion has the density of 100 mM, pH variation in association with the acetic acid gas of 1 ppm or less is not so great, as compared to the case in which the initial acetate ion has the density of 3 mM. However, because a pH value is maintained at approximately '5' even when the acetic acid of the external environment has the density of 10 ppm, it can be expected that pH variation is measured even in the gas environment of a high-density acetic acid of 10 ppm or higher.

The graph of FIG. 12 shows pH variation changing with the density of acetic acid gas when the density of initial acetate ion of the buffer solution is fixed to 30 mN and an initial pH value of the buffer solution is changed.

Referring to FIG. 12, assuming that the initial pH value of the buffer solution is set to 4, a pH value of the buffer solution is reduced to 4 or less when the acetic acid gas of 3 ppm or higher is present, so that it can be recognized that the measurement range of the acetic acid gas is set to 3 ppm or higher. Assuming that the initial pH value of the buffer solution is set to 5, a pH value of the buffer solution is reduced to 5 or less when the acetic acid gas of 1 ppm or higher is present, so that it can be recognized that the measurement range is set to 3 ppm or higher. If the initial pH value of the buffer solution is set to 6, 7 and 8, similar waveforms can be obtained.

As can be seen from FIGS. 11 and 12, a composition of the buffer solution can be decided. That is, the density of initial acetate ion and the initial pH of the buffer solution can be determined according to a desired sensing resolution and a desired sensing range, the composition ratio of the buffer solution is determined in consideration of the usage and used environment of gas sensor, so that the optimum sensing resolution and the optimum sensing range can be implemented. For example, in order to measure the acetic acid, sodium acetate in which the acetate ions having the density of 1 mM-1000 mM are dissolved can be used as the buffer solution. Most reagents including sodium acetate and acetate ions may be used as the buffer solution.

Although the above-mentioned description has exemplarily used the acetic acid as the target gas for convenience of description, it should be noted that the same description can also be applied to volatile organic acid instead of the acetic acid. Therefore, even in the case in which the target gas is the volatile organic acid but not the acetic acid, the initial pH and the density of conjugate base of the pre-dissolved volatile organic acid are appropriately adjusted, so that a desired sensing range and a desired sensing resolution can be implemented. Meanwhile, the conjugate base pre-dissolved is not always identical to the conjugate base of the target gas. In accordance with the Henderson-Hasselbalch expression shown in Equation 2, it may be possible to pre-dissolve the conjugate ions of a specific material having the same pKa as the target gas. For example, if the target gas is the volatile organic acid, the conjugate base of the material having the same pKa as in the corresponding volatile organic acid may be pre-dissolved.

In addition, a pH of the detection solution is changed when not only the acetic acid but also other volatile organic acids generated in the ripening process of kimchi react with the detection solution, sodium carbonate, sodium bicarbonate, aluminum citrate, etc. may be used as the buffer solution to measure the overall volatile organic acid. However, the sodium acetate, the sodium carbonate, the sodium bicarbonate, sodium citrate, etc. are merely exemplary, the buffer solution having a pKa value of 3~10 may be used as a buffer solution shown in the disclosure.

Although the initial pH of the buffer solution may be changed according to a desired sensing range, the initial pH is higher than the pKa value of the target gas. For example, if the target gas is the volatile organic acid, the initial pH of the buffer solution is set to 6 or higher so that the volatile organic acid can be measured in the large density range.

If the target gas is dissolved in the detection solution, the pH value of the detection solution is changed. Thus, the pH indicator having a color being changed in response to the pH variation may be used, so that it can be recognized whether the target gas is detected through the pH variation generated when the target gas is dissolved. The pH indicator is characterized in that its own color is changed in response to the degree of reaction with H2 ions contained in the solution.

That is, the pH value of the detection solution is changed because the target gas is dissolved in the detection solution, and the color of the pH indicator is also changed in response to the changed pH. As a result, if the color of the detection solution is changed, it can be recognized that the corresponding target gas has been detected and the corresponding target gas has been generated in the target food (O).

The pH indicator may be set to a pH indicator, the color of which is changed within the pH range when each target gas is dissolved in solvent. If necessary, one or more pH indicators may be used.

For example, the detection solution of the detection unit 120 for detecting the acetic acid may include a bromothymol blue pH indicator and a methyl red pH indicator. Bromothymol blue pH indicator is discolored from blue to yellow when a pH value is reduced from 7.6 to 6.0. Methyl red pH indicator is discolored from yellow to red when a pH value is reduced from 6.0 to 4.8. If the detection unit 120 for detecting the acetic acid reacts with the acetic acid, the bromothymol blue is blue in color when a pH is set to 7.6. Thereafter, if the pH value reaches 6.0, the bromothymol blue is changed to yellow in color, so that the yellow color appears. If the pH value is set to 6.0, the methyl red is yellow in color, so that the yellow color appears. Thereafter, if the pH value is set to 4.8, the methyl red is changed to red in color, so that the red color appears. In other words, if the color of the detection unit 120 for detecting the acetic acid is sequentially changed in the order of blue→yellow→red, it can be recognized that the density of acetic acid emitted from the target food (O) increases, and it can also be recognized that kimchi is gradually ripening when the target food is kimchi. The bromothymol blue pH indicator and the methyl red pH indicator may be simultaneously used, or may also be used independently of each other. As other pH indicators, chlorophenol red indicator may be used. Because chlorophenol red is red in color when the pH value is 6.5, the detection unit indicates a red color. Thereafter, if the pH value is changed to 4.5, the chlorophenol red is changed to yellow in color, so that the detection unit indicates a yellow color. The chlorophenol red may be used independently, or may also be used simultaneously with the bromothymol blue as necessary.

As described above, the detection solution may include a solvent in which the target gas can be dissolved and a pH indicator for colorfully indicating pH variation based on dissolution of the target gas. In addition, the detection solution may further include a moisture absorbent to suppress moisture evaporation of the detection solution as well as to reduce the moisture sorbent. For example, the moisture absorbent may include any one of glycerin, ethylene glycol, polyethylene glycol, calcium chloride, sodium chloride, etc.

Figure 13:
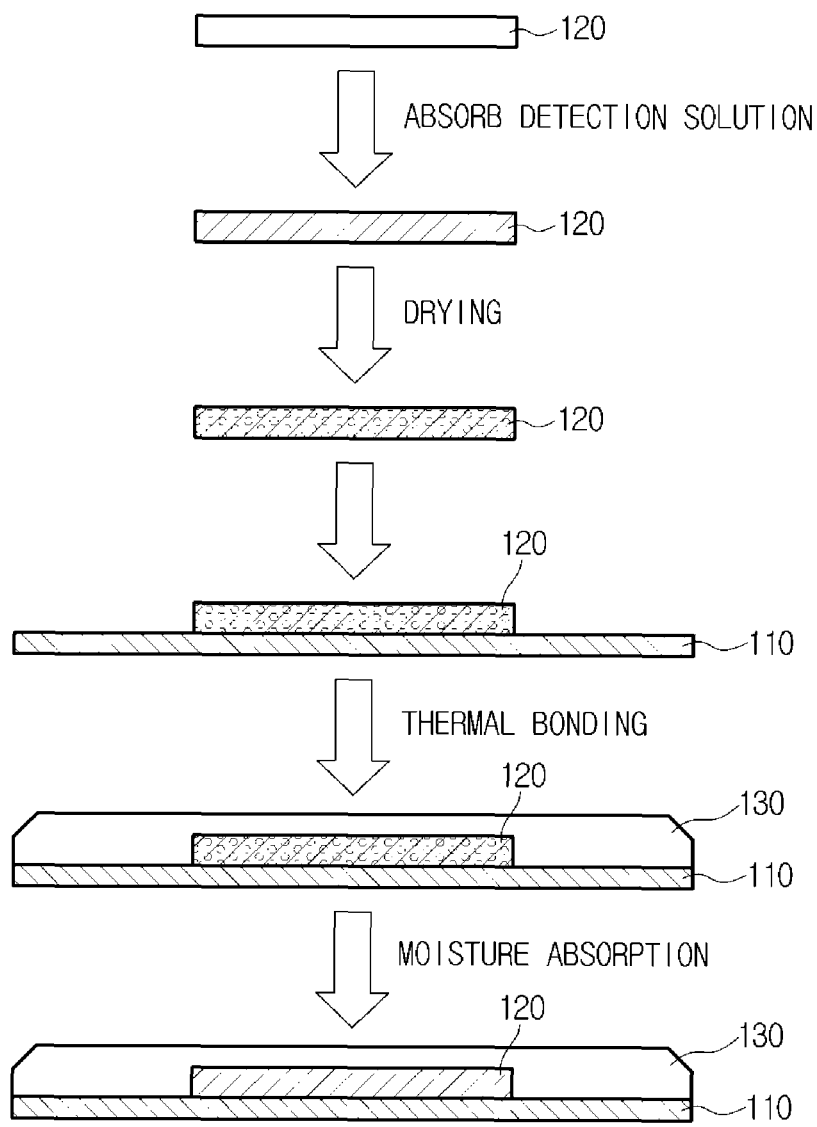
FIG. 13 is a conceptual diagram illustrating a method for manufacturing a gas sensor according to an embodiment of the disclosure.

As described above, the gas sensor 100 according to an embodiment may include a base 110, a hydrophilic membrane, and a transparent membrane 130. A method for manufacturing the gas sensor 100 is shown in FIG. 13. FIG. 13 is a conceptual diagram illustrating a method for manufacturing the gas sensor 100 according to an embodiment. Referring to FIG. 13, a predetermined amount of detection solution including the pH indicator and the like drops to the hydrophilic membrane, and is thus absorbed into the hydrophilic membrane. The hydrophilic membrane in which the detection solution is absorbed is heated at a temperature of approximately 80° C. for approximately 30 seconds, so that the hydrophilic membrane is dried. The process for drying the hydrophilic membrane is used when the membrane 130 is attached to the hydrophilic membrane. That is, a moisture evaporation process is used when the transparent membrane 130 is heat-bonded to the hydrophilic membrane.

If the hydrophilic membrane is dried, the dried hydrophilic membrane is placed on the base 110, the hydrophilic membrane is covered with the transparent membrane 130, and the transparent membrane 130 and the hydrophilic membrane are heat-bonded to each other. If the manufactured gas sensor 100 is installed in a food container or a refrigerator, the moisture absorbent contained in the detection solution absorbs the peripheral water vapor in such a manner that there occurs a reaction of the pH indicator in which reaction proceeds under the presence of moisture. If the moisture absorbent absorbs the peripheral water vapor so that the hydrophilic membrane includes moisture, the detection solution reacts with the target gas, so that the pH indicator is discolored in response to the changing pH value.

A user confirms the degree of discoloration of the gas sensor 100 so that the user can recognize the ripening degree of kimchi. In this case, information regarding the kimchi ripening degree corresponding to the changed principal color of the gas sensor 100 is previously provided to the user, so that the user can utilize the received information as needed. The user compares the color of the actual gas sensor 100 with the color of information indicating the kimchi ripening state, so that the user can recognize the kimchi ripening state without opening the container including kimchi.

The user observes color change of the detection unit 120 of the gas sensor with the naked eye so that the user can confirm the ripening degree of the target food (O). However, the user may have difficulty in visually recognizing slight color change of the detection unit 120 so that it may be difficult to recognize the category of food or the degree of freshness of food on the basis of discoloration information of the gas sensor 100.

In order to address the above-mentioned issues, the gas sensor according to an embodiment of the disclosure may further include an image detection unit 140 configured to acquire an image regarding color change of the above-mentioned gas sensor.

Figure 14:
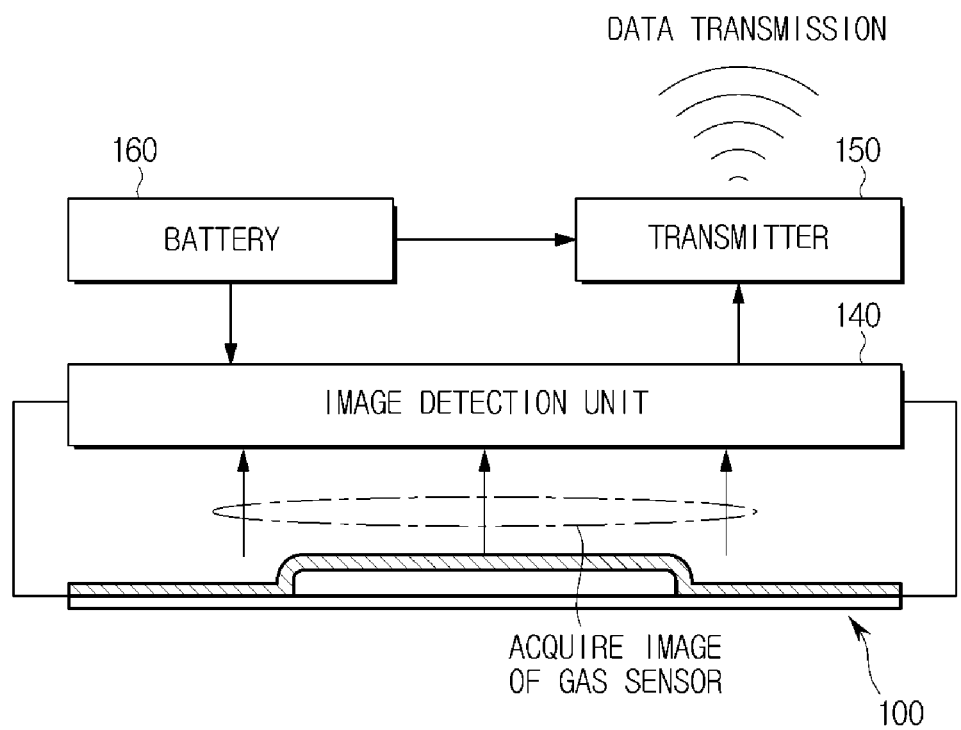
FIG. 14 is a conceptual diagram illustrating a gas sensor according to an embodiment of the disclosure.
Figure 15:
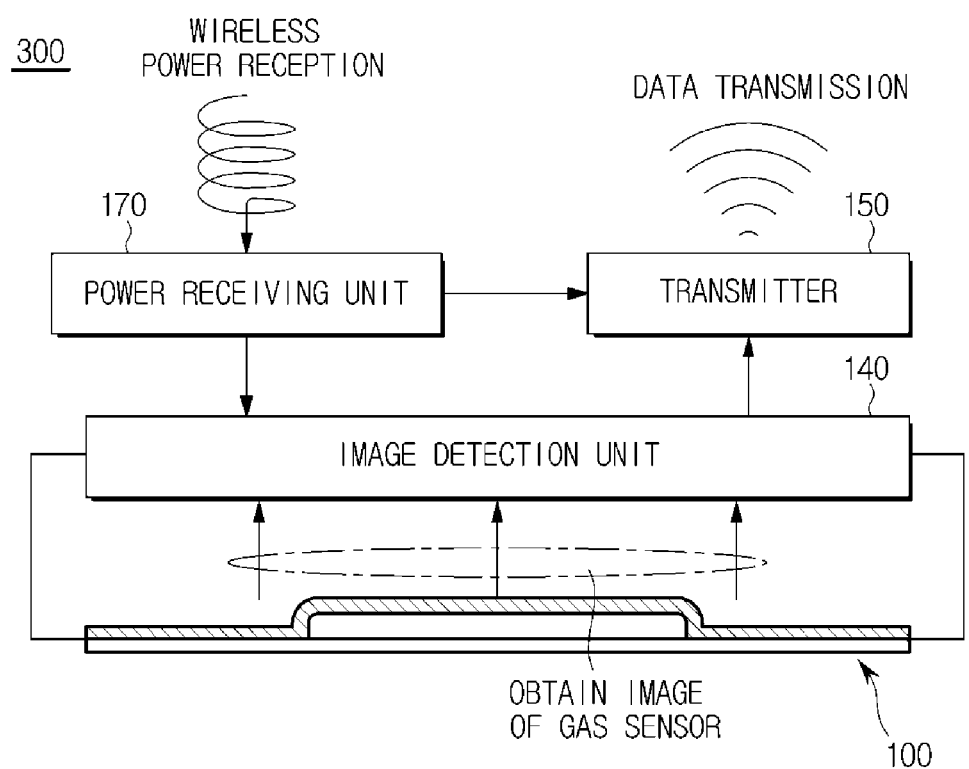
FIG. 15 is a conceptual diagram illustrating a modification example of a gas sensor according to an embodiment of the disclosure.

FIG. 14 is a conceptual diagram illustrating the gas sensor according to an embodiment of the disclosure. FIG. 15 is a conceptual diagram illustrating a modification example of the gas sensor according to an embodiment of the disclosure.

Referring to FIG. 14, the gas sensor 300 according to an embodiment may include a gas sensor 100 of FIG. 3, an image detection unit, or detector, 140 for obtaining an image regarding the color change; a transmitter 150 for transmitting the gas-sensor image data obtained by the image detection unit 140 to an external part; and a battery 160 for providing a power source to operate the image detection unit 140 and the transmitter 150.

The image detection unit 140 may use a photodiode, a CMOS image sensor, and a CCD. The image detection unit 140 may obtain images of the gas sensor to detect color change of the detection unit 120 contained in the gas sensor 100. The image detection unit 140 may successively obtain the images of the gas sensor 100, and may obtain data regarding the color change by sampling the acquired images. Alternatively, the image detection unit 140 may obtain data of the color change by obtaining the image of the gas sensor 100 at intervals of a predetermined time.

The obtained data may be transmitted to the external device having a receiver through the transmitter 150. The external device may analyze data received from the gas sensor 300, and may determine a state of the target food (O). Various communication schemes between the transmitter 150 of the gas sensor 300 and the receiver of the receiver may be used.

The battery 160 may provide a power source for operating the image detection unit 140 and the transmitter 150. The battery 160 may be various commercial disposable batteries or rechargeable batteries.

Alternatively, as can be seen from the medication example of an embodiment of FIG. 15, the gas sensor 300 may include a power receiving unit, or receiver, 170 capable of being wirelessly rechargeable using a wireless power transmission technology instead of using the battery 160 of FIG. 14. The power receiving unit 150 may be configured to be appropriate for various wireless power transmission schemes, for example, a magnetic induction scheme, a magnetic resonance scheme, an electromagnetic wave scheme, etc.

The gas sensor according to an embodiment may obtain the color change data of the gas sensor 100 using the image detection unit 140, may transmit the obtained color change data to the external device having a data analysis function, and thus allow the external device to determine a state of the target food (O). If the external device, for example, the refrigerator, analyzes data received from the gas sensor 300, displays a state of the target food (O) through a display unit, or display, or the like, the user can recognize a state of the target food (O) without viewing the color change of the gas sensor 300 with the naked eye. Alternatively, a mobile device, such as a smartphone or a tablet computer, may analyze data received from the gas sensor 300, and may inform the user of the state of the target food (O) through the display unit. Furthermore, the user may also control a temperature of the refrigerator storing the target food (O) therein using the mobile device. A detailed description thereof will hereinafter be given in detail.

The gas sensors (100, 300) according to the embodiment may be mounted to the container storing the food therein.

Figure 16:
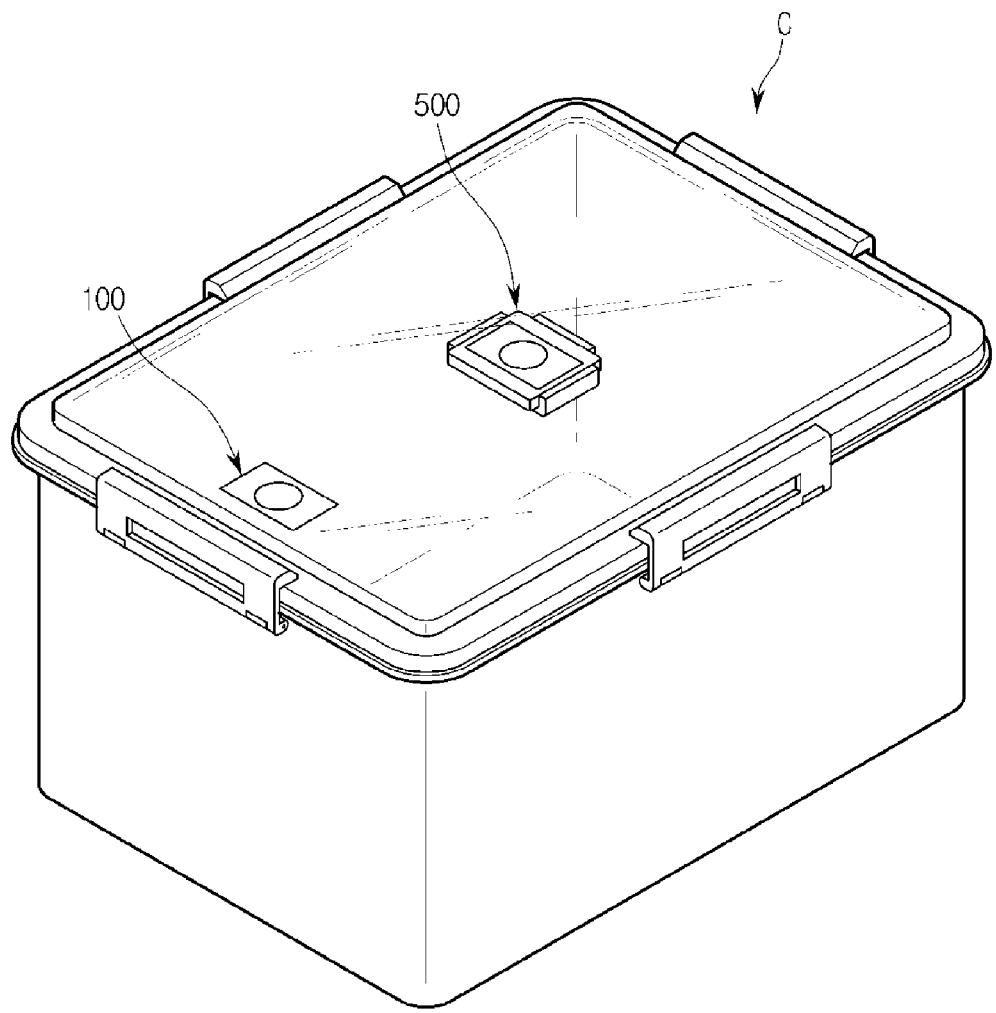
FIG. 16 is a diagram illustrating a gas sensor mounted to a transparent part of a container according to an embodiment of the disclosure.
Figure 17:
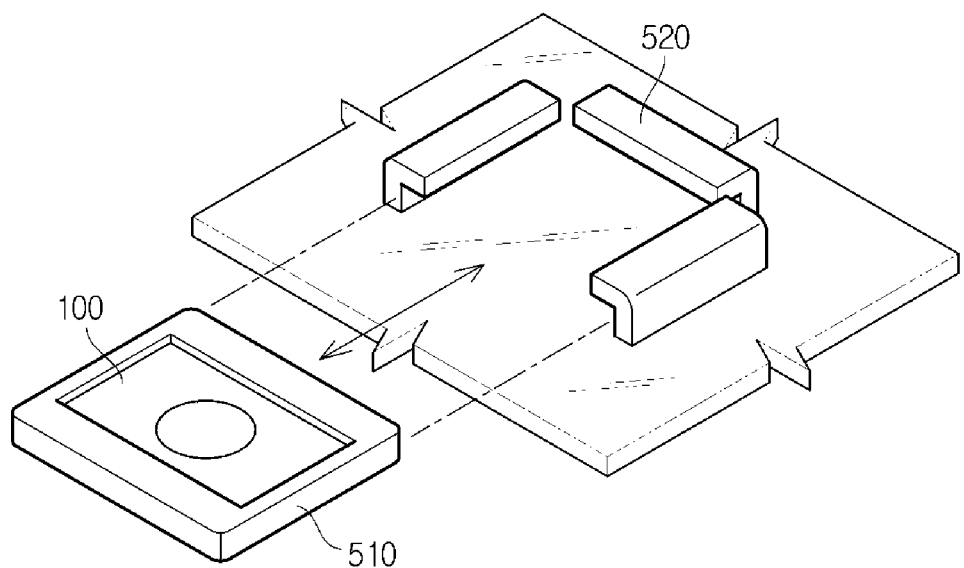
FIG. 17 is a diagram illustrating a support unit for mounting a gas sensor to a transparent part of a container according to an embodiment of the disclosure.

FIG. 16 is a diagram illustrating the gas sensor mounted to a transparent part of a container according to an embodiment of the disclosure. FIG. 17 is a diagram illustrating a support unit, or supporter, for mounting the gas sensor to a transparent part of the container according to an embodiment of the disclosure.

If the container (C) of the food has a transparent part or a partially transparent part, the transparent membrane 130 contained in the gas sensor 100 of an embodiment is attached to the inner wall of the transparent part of the container C in such a manner that the target food (O) and the base 110 face each other. The gas sensor 100 according to an embodiment has a patch format, so that the gas sensor may be attached to the inner wall using a predetermined adhesive material. The gas sensor 300 according to an embodiment includes various electronic components, such as the image detection unit 140, the transmitter 150, and the battery 160, so that it may be undesirable that the gas sensor 300 be directly attached to the inner wall on which the target food (O) is placed.

The gas sensor 100 is not directly attached thereto, a predetermined support unit 520 for installation of the gas sensor 100 may be provided at the inner wall of the transparent part of the container (C), and the gas sensor 100 may also be installed at the support unit 520 (See reference number 500).

The support unit 520 of FIG. 17 may enable the gas sensor 100 to be detachably coupled through slide coupling. The support unit 520 is configured in the form of "∟" shape, and may be attached to a transparent wall of the container C. Although three support units 520 are shown in FIG. 17, there is no limitation in the number of support units 520. The gas sensor 100 may be slidably coupled or separated along the support unit 520.

The gas sensor 100 according to an embodiment is configured in the form of a patch and is formed of a flexible material. As can be seen from FIG. 17, after the gas sensor 100 is mounted to the slide member 510 having suitable stiffness so that the gas sensor 100 can be appropriately mounted to the support unit 520, the slide member 510 is then mounted to the support unit 520 so that the gas sensor 100 can be mounted to the container C. The structure or shape of the support unit 520 shown in FIG. 17 is shown as an example, and various other structures or shapes can also be applied to the support unit 520 without departing from the scope or spirit of the disclosure.

Figure 18:
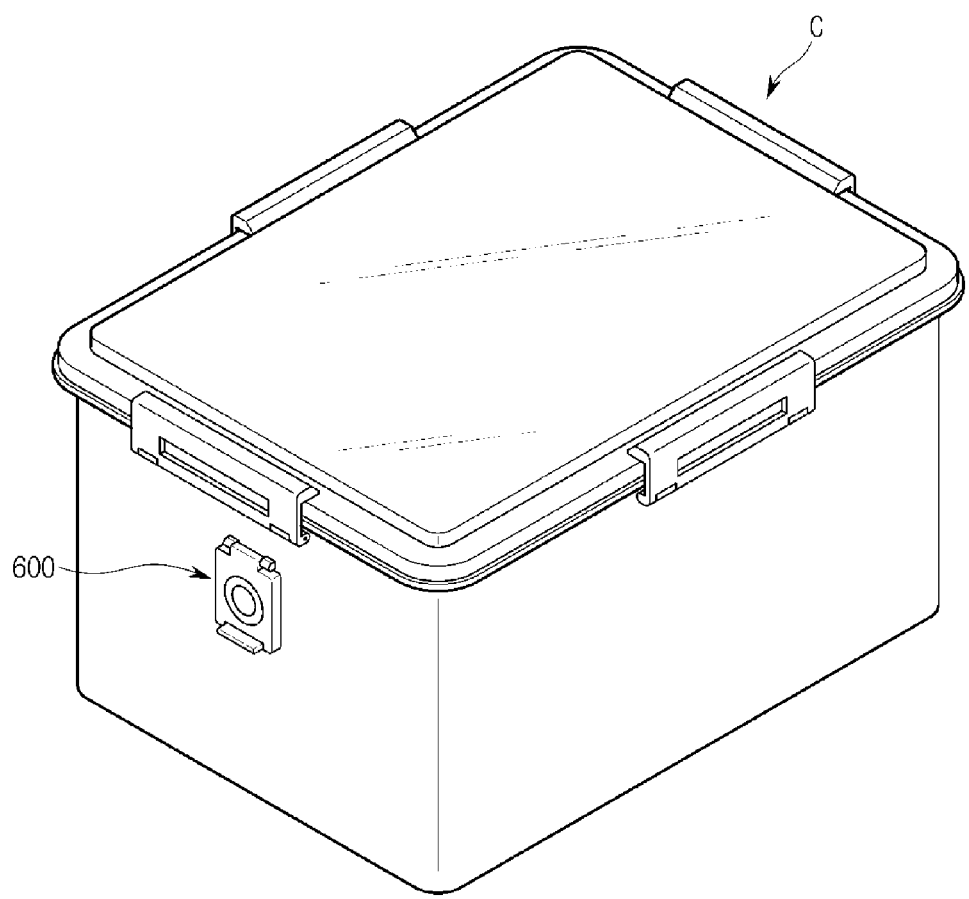
FIG. 18 is a diagram illustrating a gas sensor mounted to an opaque part of a container according to an embodiment of the disclosure.
Figure 19:
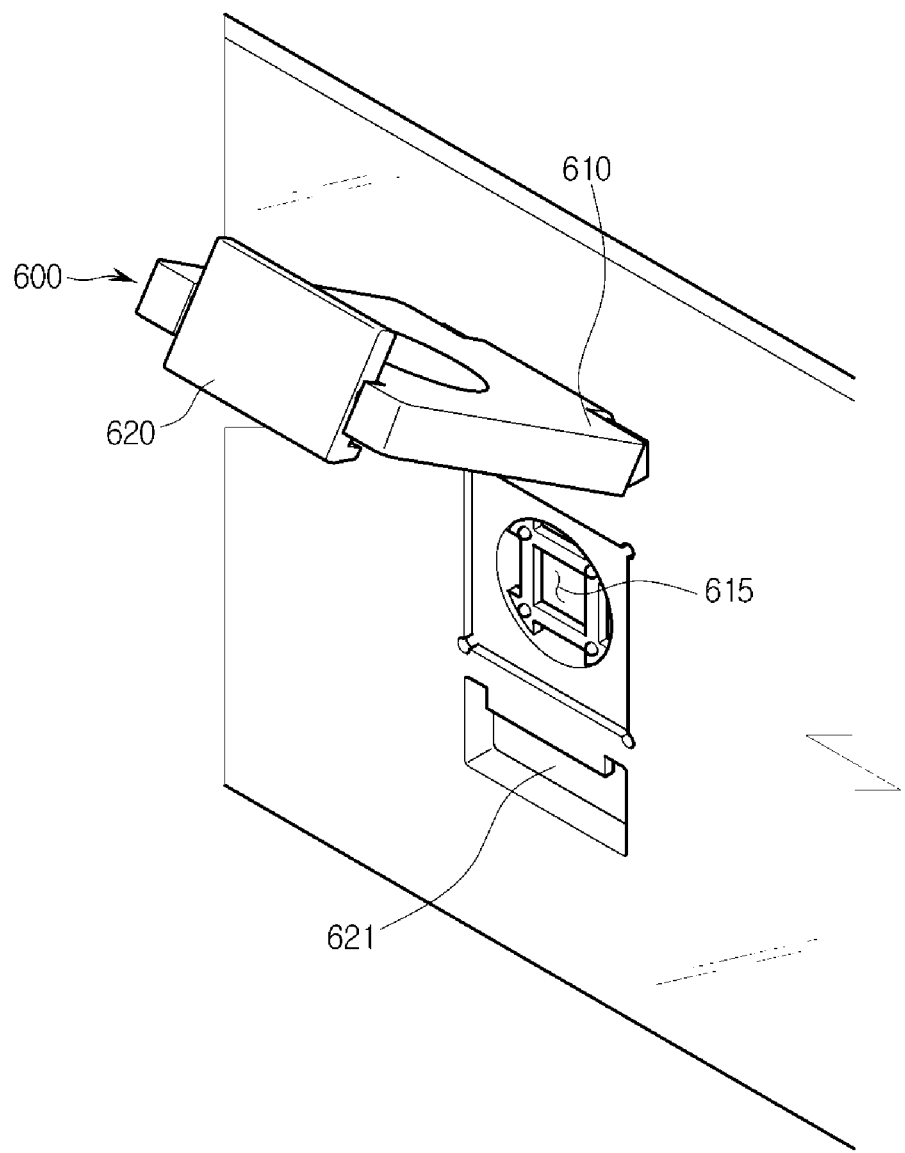
FIG. 19 is a diagram illustrating that an instrument unit having a gas sensor is hinge-coupled to an opaque part of a container according to an embodiment of the disclosure.
Figure 20:
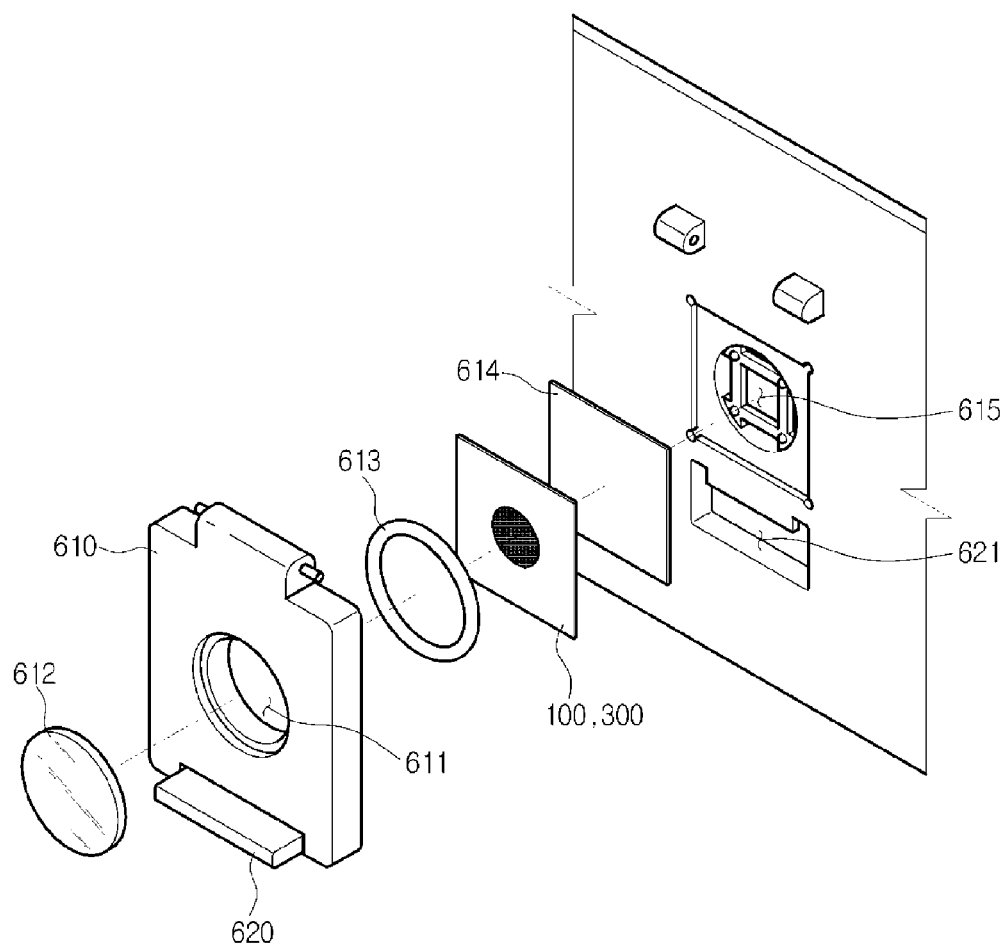
FIG. 20 is an exploded perspective view illustrating an instrument unit having a gas sensor according to an embodiment of the disclosure.

FIG. 18 is a diagram illustrating a gas sensor mounted to an opaque part of a container C according to an embodiment of the disclosure. FIG. 19 is a diagram illustrating that an instrument unit having a gas sensor is hinge-coupled to an opaque part of the container C according to an embodiment of the disclosure. FIG. 20 is an exploded perspective view illustrating an instrument unit having the gas sensor according to an embodiment of the disclosure.

If the gas sensor 100 is mounted to the inner wall of the opaque part of the container C, it is impossible for the user to visually observe color change of the gas sensor 100. The gas sensor 300 according to an embodiment can be installed in the container C because the image detection unit 140 obtains an image of the gas sensor 100. However, as described above, the gas sensor 300 according to an embodiment includes various electronic components such as an image detection unit 140, a transmitter 150, and a battery 160, so that it is undesirable that the gas sensor 300 be directly mounted to the inner wall to which the target food O will be mounted.

In accordance with the embodiments, a hole 615 is formed at an opaque part of the container C in which the gas sensors (100, 300) will be installed, and the gas sensors (100, 300) are installed in the hole 615. If the gas sensors (100, 300) are installed as described above, the gas sensors (100, 300) may detect the gas generated from the target food O accommodated in the container C through the hole 615, and the user may directly observe color change of the gas sensors (100, 300).

As can be seen from FIG. 18, the gas sensors (100, 300) are mounted to a predetermined instrument unit 600. As can be seen from FIG. 19, the instrument unit 600 may be hinge-coupled to the wall of the container C having a hole. A fixing groove 621 may be provided at the bottom of the hole-included part, so that the instrument unit 600 can be fixed to the container C when being brought into contact with the wall of the container C.

As can be seen from FIG. 20, the instrument unit 600 may include a main body 610 having a hole 611 in which the gas sensors (100, 300) are installed. Here, the hole 611 is located at the center of the main body 610. A fixing unit 620 coupled to the fixing groove 621 of the wall of the container C is provided at the bottom of the main body 610. Thus, when the instrument unit contacts the wall of the container C, the instrument unit 600 can be fixed to the wall of the container C through the fixing unit 620.

A transparent cover 612 may be installed in the hole 611 of the main body 610 so that the transparent cover 612 can prevent external impurities from reaching the gas sensors (100, 300). In order to prevent leakage of fluid through the hole 611 of the instrument unit 600, the O-ring 613 formed of a rubber material may be installed in the hole 611 of the instrument unit 600 as shown in FIG. 20. If the gas sensors (100, 300) are mounted to the hole 611, an additional gas permeable layer 614 is selectively installed, and the instrument unit 600 is hinge-coupled to the wall of the container C including a hole 615. The structures, shapes, and constructions of the instrument unit 600 shown in FIGS. 18 to 20 are merely exemplary, and it should be noted that other structures, other shapes, and other constructions may also be applied to the instrument unit 600 without departing from the scope or spirit of the disclosure. The container shown in FIGS. 18 to 20 may also be used as a gas detection container capable of detecting the target gas emitted from a target object accommodated in the container.

FIGS. 21 to 24 are diagrams illustrating the appearance of the gas sensor mounted to a container according to an embodiment of the disclosure.

Figure 21:
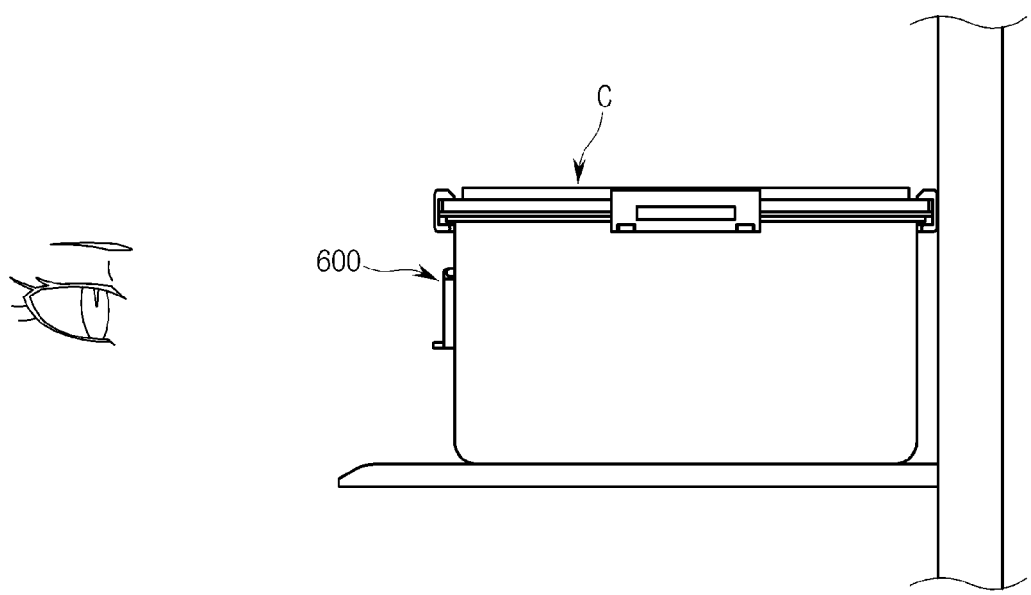
FIGS. 21, 22, 23, and 24 are diagrams illustrating the observation appearance of a gas sensor mounted to a container according to an embodiment of the disclosure.

If the container coupled to the gas sensors (100, 300) as shown in FIGS. 18 to 20 is placed on a shelf of the refrigerator and the shelf is inserted to accommodate the container into the refrigerator as shown in FIG. 21, the user can observe color change of the gas sensors (100, 300) with the naked eye.

Figure 22:
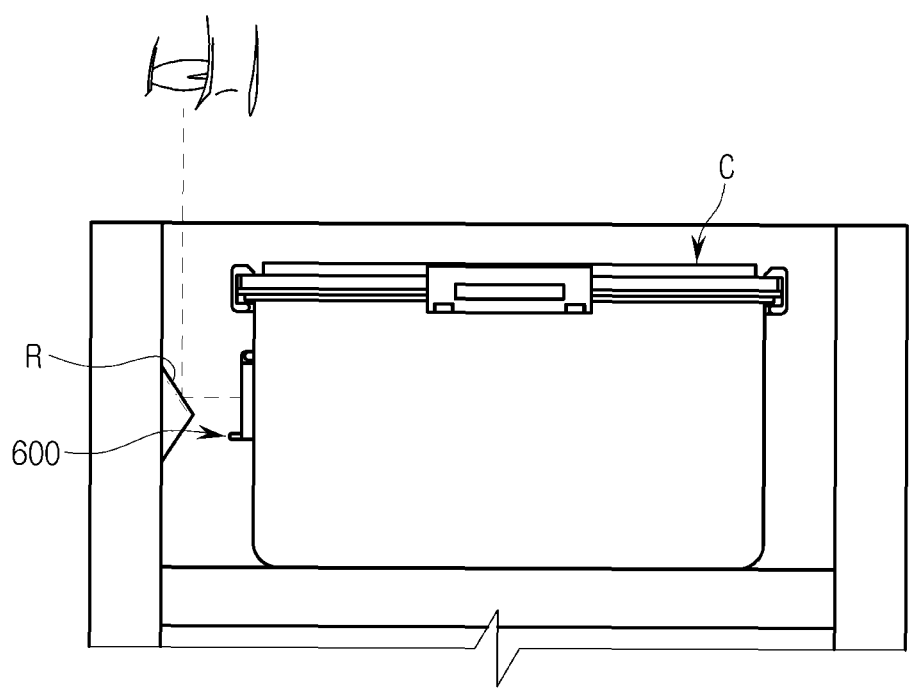

However, in the case of using the refrigerator shown in FIG. 22 in which the container C is put on the bottom of the storage chamber, instead of using the refrigerator shown in FIG. 21 in which the container C placed on a shelf is inserted into the refrigerator, the user is unable to directly observe the color change of the gas sensors (100, 300). In this case, as shown in FIG. 22, a reflector R capable of reflecting images of the gas sensors (100, 300) is mounted to the wall of the storage chamber facing the gas sensors (100, 300), the user can observe color change of the gas sensors (100, 300) from the images of the gas sensors (100, 300) reflected from the reflector R.

Figure 23:
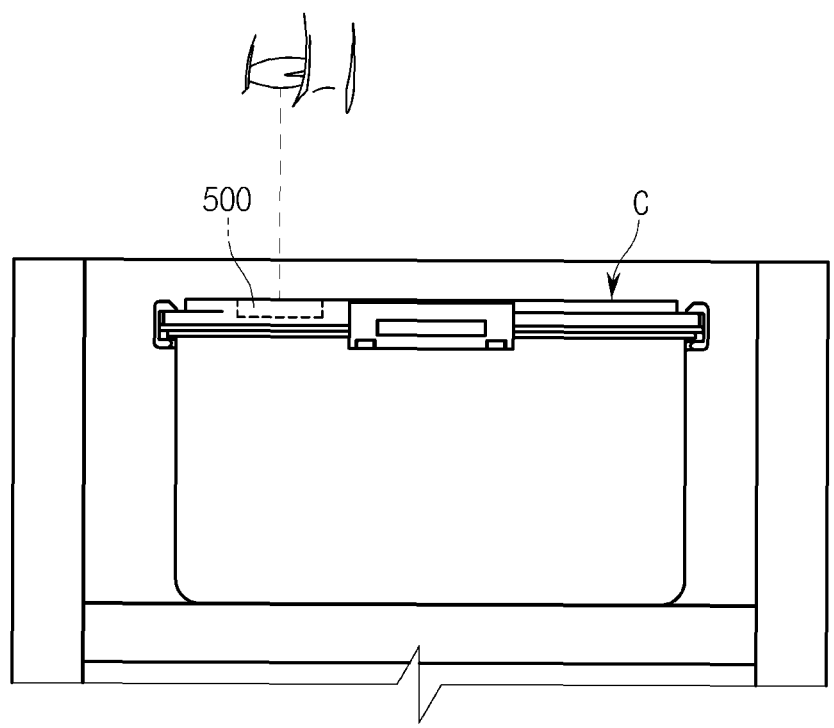

If the container C including the gas sensor 100 as shown in FIGS. 16 and 17 is accommodated in the refrigerator shown in FIG. 23 in which the container C is put on the bottom of the storage chamber, the user can observe the color change of the gas sensor 100 with the naked eye.

Figure 24:
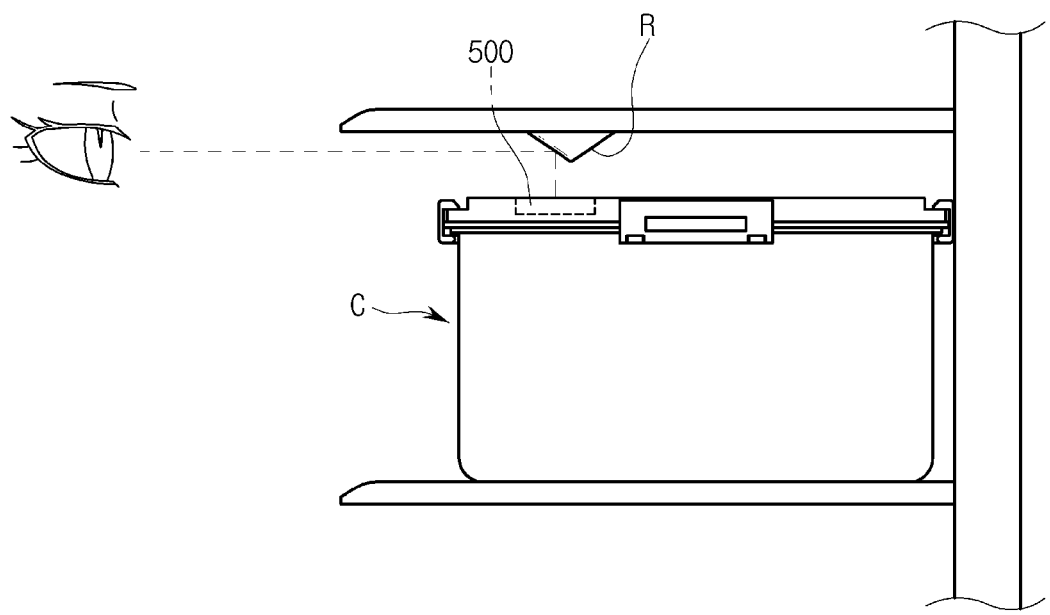

However, in the case of using the refrigerator shown in FIG. 24 in which the container C placed on a shelf is inserted into the refrigerator, instead of using the refrigerator in which the container C is put on the bottom of the storage chamber, the user is unable to directly observe color change of the gas sensors (100, 300).

Figure 25:
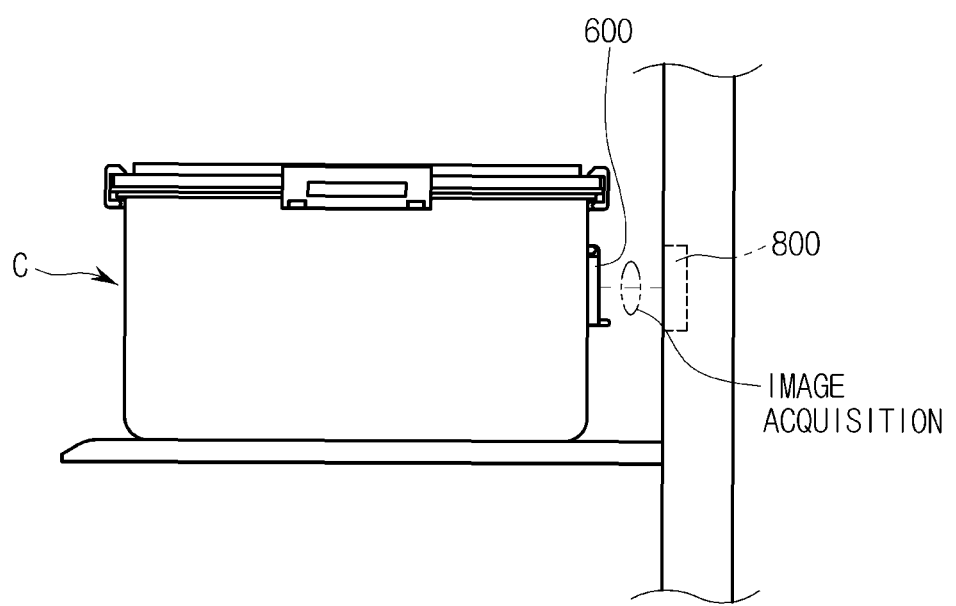
FIGS. 25 and 26 are diagrams illustrating an image sensor for use in a refrigerator to obtain an image of a gas sensor according to an embodiment of the disclosure.
Figure 26:
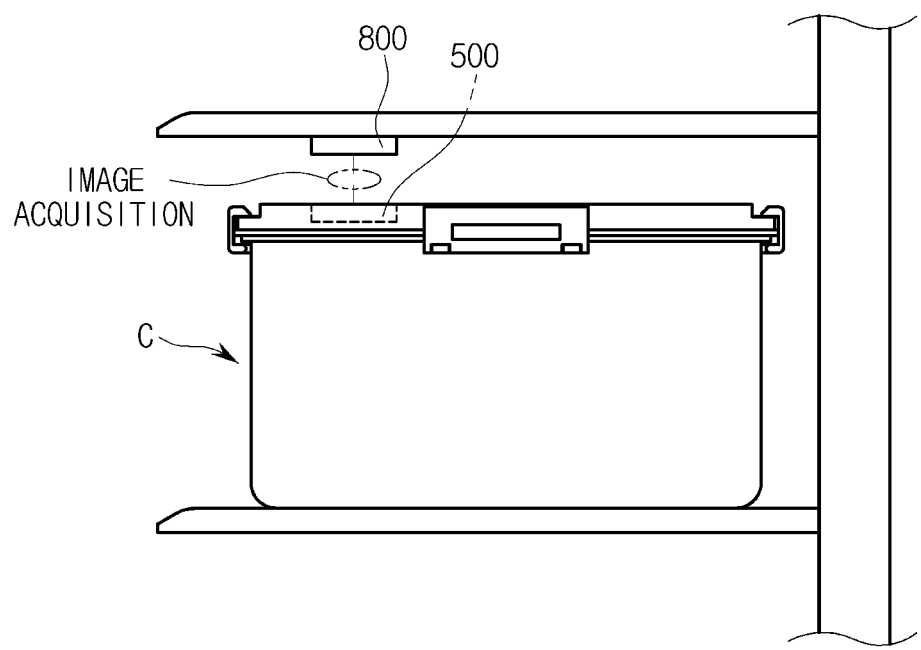

In this case, as shown in FIG. 24, the reflector R capable of reflecting the image of the gas sensor 100 is installed at the bottom of the shelf facing the gas sensor 100, so that the user can observe color change of the gas sensor 100 from the image of the gas sensor 100 reflected through the reflector R. The user may not directly observe the color change of the gas sensor, instead detecting the color change of the gas sensor by obtaining the gas sensor image from the image sensor mounted to the refrigerator. FIGS. 25 and 26 are diagrams illustrating an image sensor for use in a refrigerator to obtain an image of a gas sensor according to an embodiment of the disclosure.

The refrigerator applied to this embodiment may be a kimchi refrigerator configured to store kimchi therein or a general refrigerator. In addition, the refrigerator may be classified into an upright refrigerator and a cover-type refrigerator (hereinafter referred to as a covered refrigerator). The upright refrigerator and the covered refrigerator may be kimchi refrigerators or general refrigerators. There is no limitation in categories and usages of the refrigerator of the disclosure and, as such, all kinds of refrigerators may be applied to the disclosure.

If the container including the gas sensors (100, 300) shown in FIGS. 18 to 20 is accommodated on the shelf of the refrigerator 900 as shown in FIG. 25, the image sensor 800 capable of obtaining the images of the gas sensors (100, 300) may be mounted to the wall of the refrigerator 900 facing the gas sensors (100, 300).

If the container C including the gas sensor 100 shown in FIGS. 16 and 17 is accommodated on the shelf of the refrigerator 900 as shown in FIG. 26, the image sensor 800 capable of obtaining the image of the gas sensor 100 may be installed at the bottom of the shelf facing the gas sensor 100.

The installation positions of the image sensors 800 shown in FIGS. 25 and 26 are merely examples, the gas sensor may be installed at any position facing the gas sensor of the container C in the refrigerator 900. In more detail, if the image acquisition available range of the image sensor 800 and the container C are accommodated in the refrigerator 900, the installation position of the image sensor 800 may be determined in consideration of the position of available gas sensor.

Figure 27:
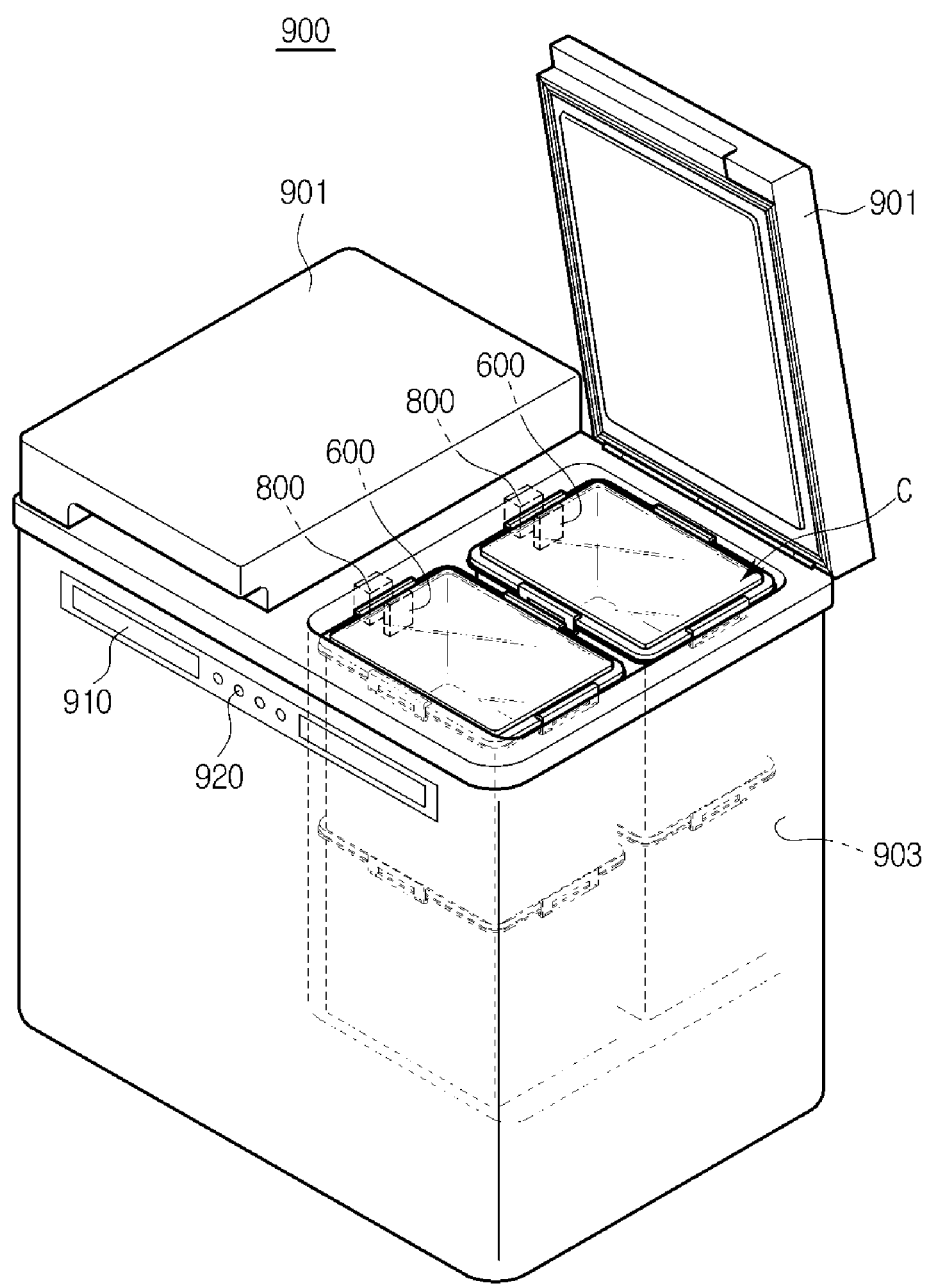
FIGS. 27 and 28 are diagrams illustrating an image sensor for use in a covered refrigerator to obtain an image of a gas sensor according to an embodiment of the disclosure.
Figure 28:
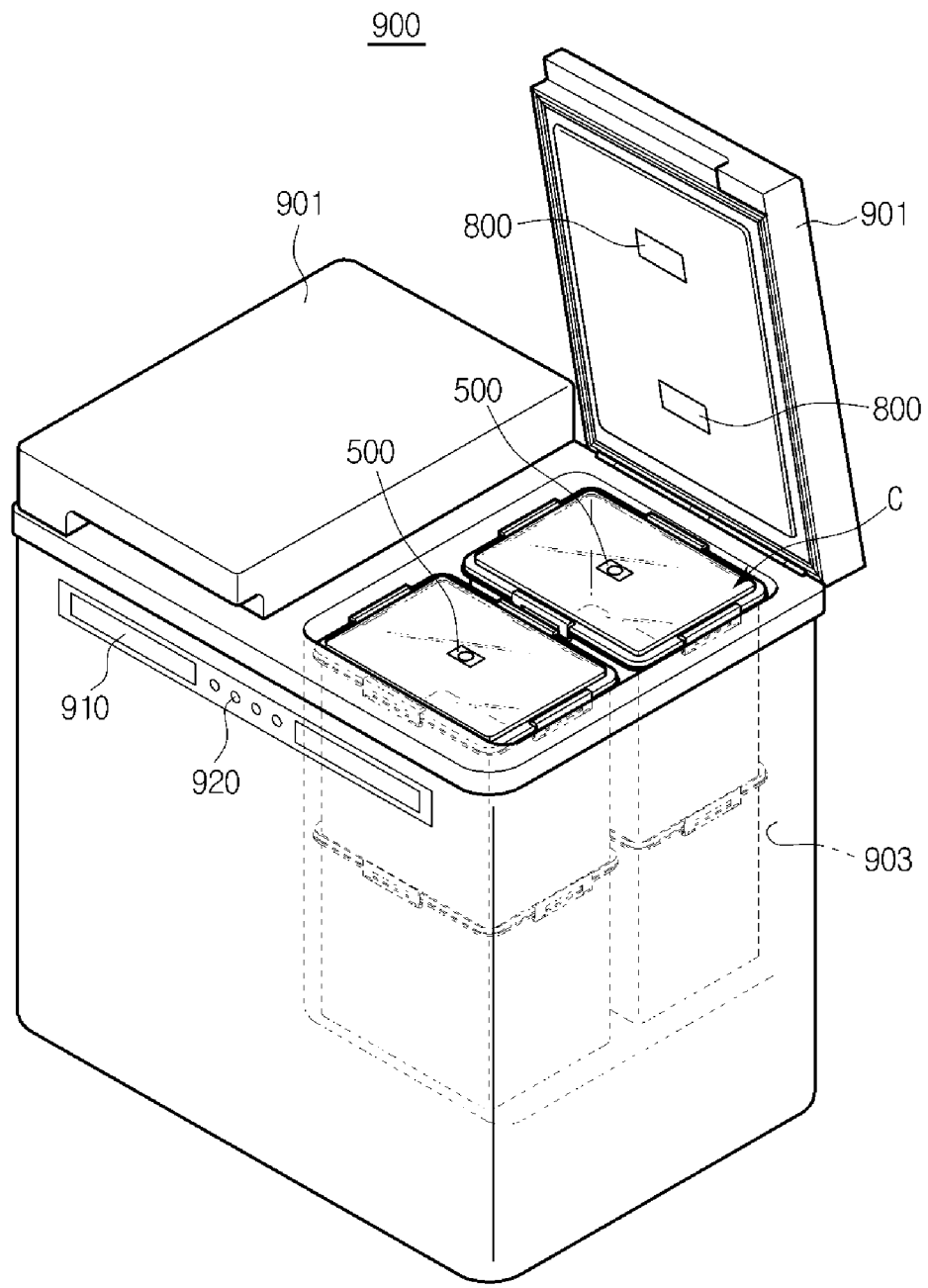

FIGS. 27 and 28 are diagrams illustrating the image sensor 800 for use in a covered refrigerator 900 to obtain an image of the gas sensor according to an embodiment of the disclosure.

Referring to FIG. 27, if the container C mounted to the gas sensors (100, 300) is accommodated in the storage chamber 903 as shown in FIGS. 18 to 20, the image sensor 800 may be installed at the wall of the storage chamber 903 so that the gas sensors (100, 300) are located to face the gas sensors (100, 300) of the container C.

In addition, as shown in FIG. 28, if the container C including the gas sensor 100 shown in FIGS. 16 and 17 is accommodated in the storage chamber 903, the image sensor 800 is installed at the inside of the refrigerator cover 901 in such a manner that the image sensor 800 can obtain the image of the gas sensor when the refrigerator cover 901 is closed.

Figure 29:
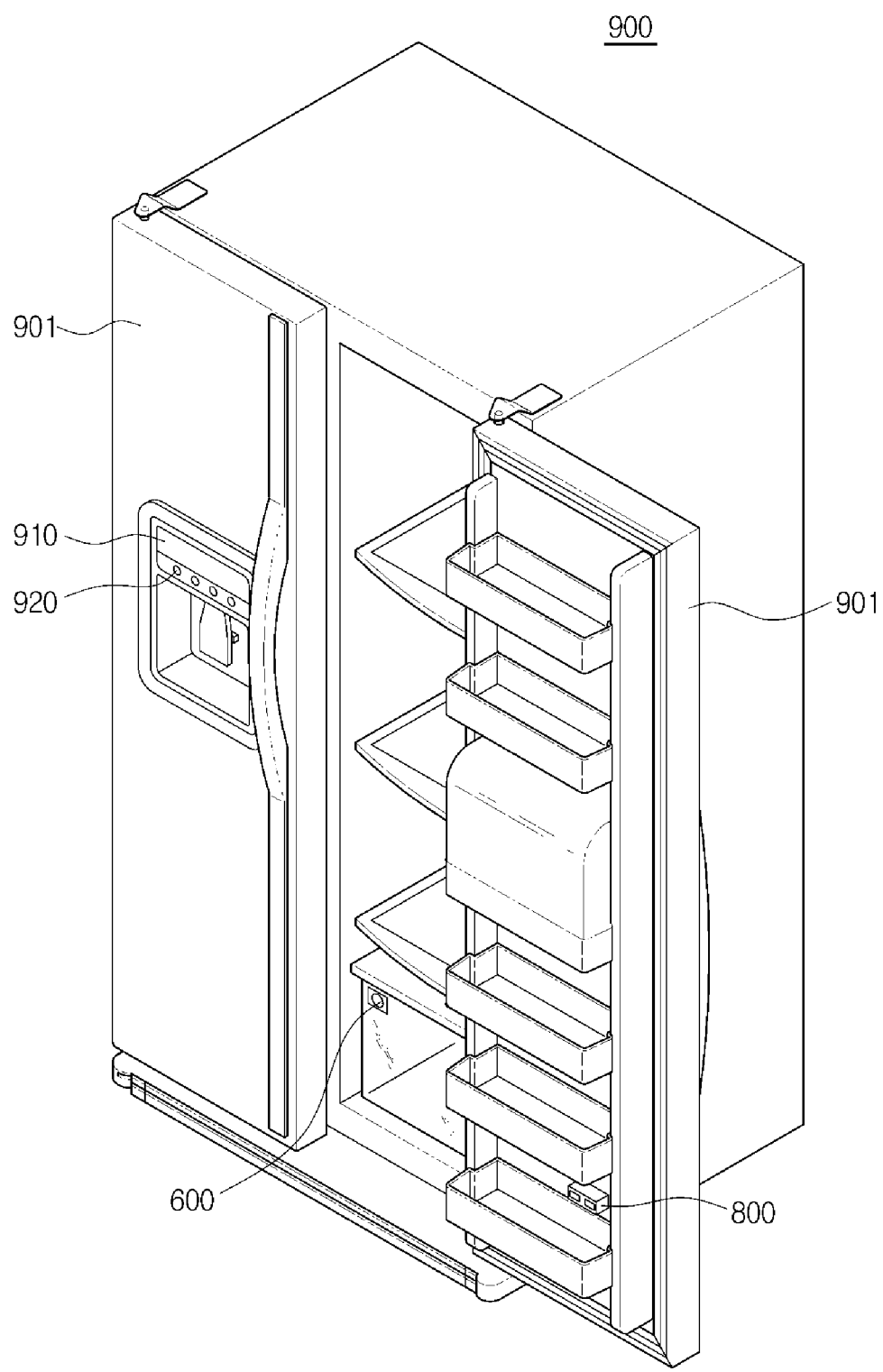
FIGS. 29 and 30 are diagrams illustrating an image sensor for use in an upright refrigerator to obtain an image of a gas sensor according to an embodiment of the disclosure.
Figure 30:
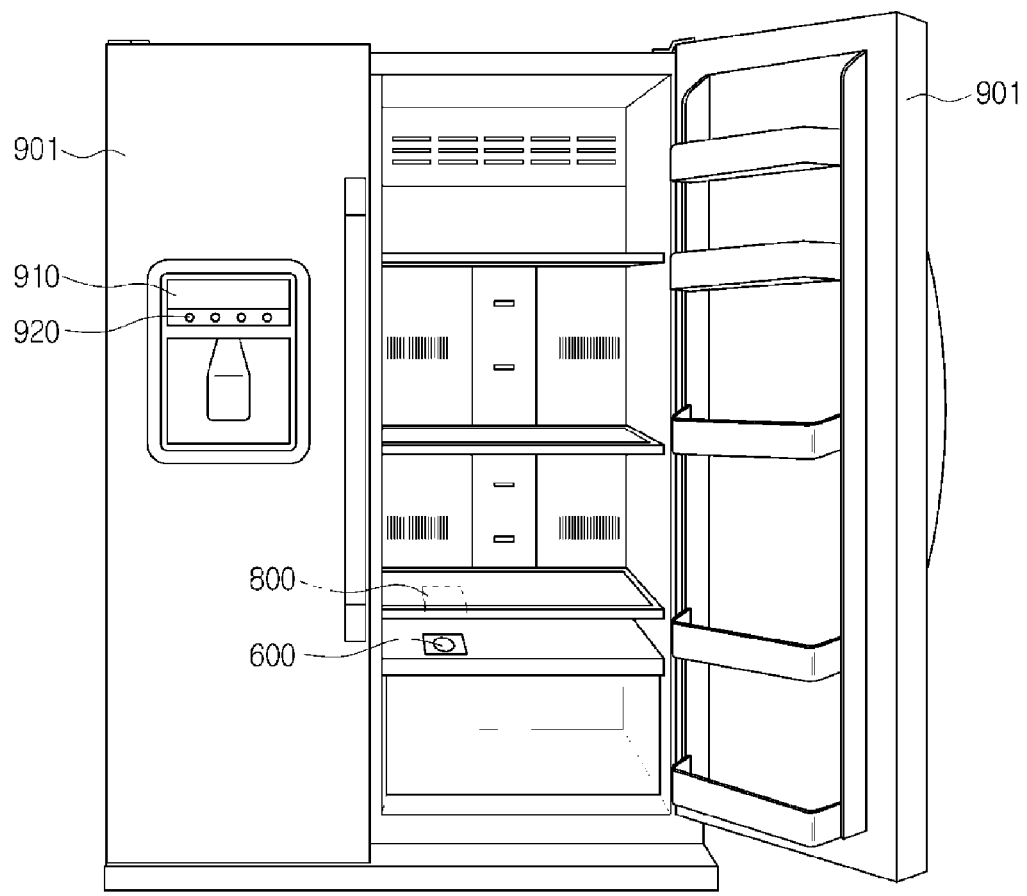
Figure 31:
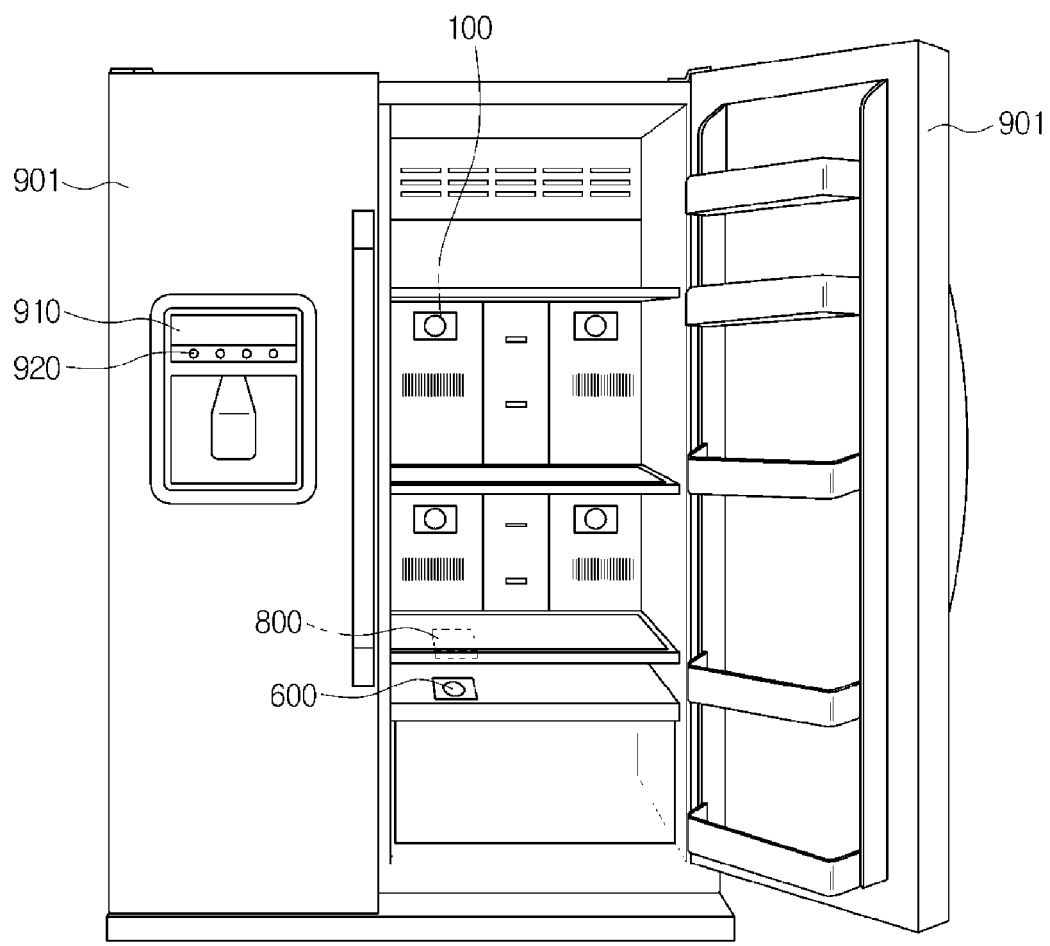
FIGS. 31 and 32 are diagrams illustrating a gas sensor and an image sensor mounted to a storage chamber divided by an internal shelf of the upright refrigerator according to an embodiment of the disclosure.
Figure 32:
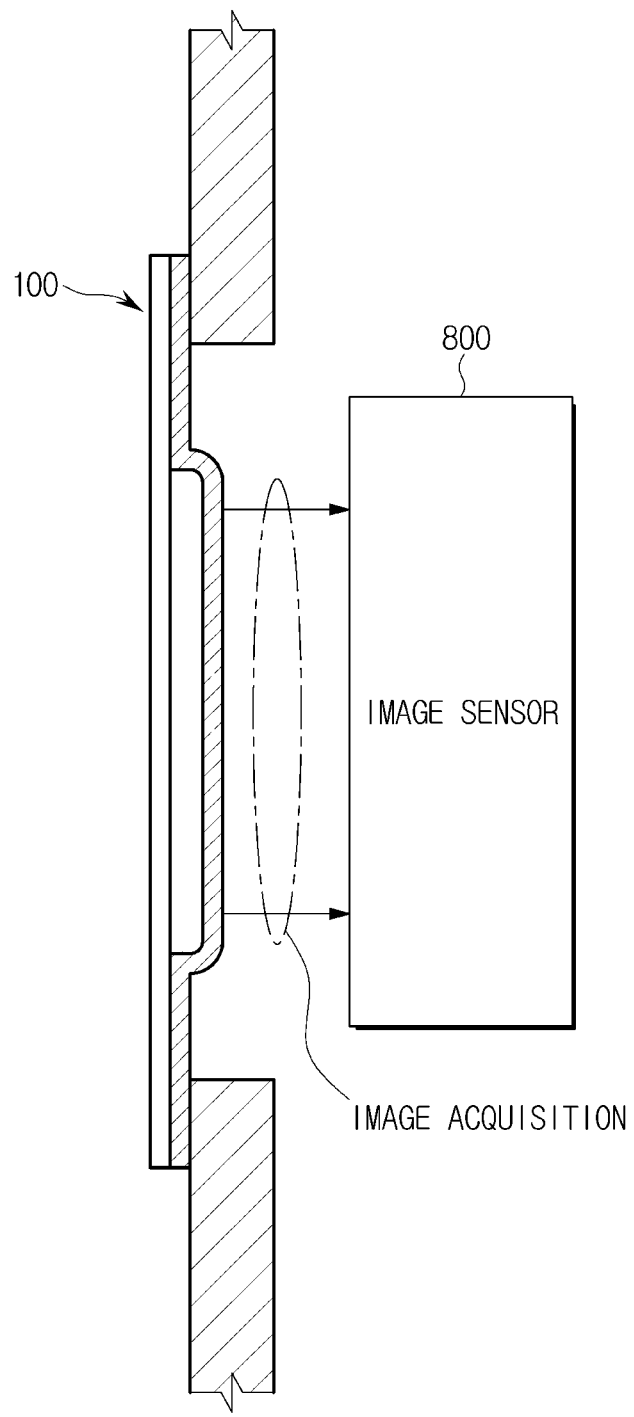

FIGS. 29 and 30 are diagrams illustrating the gas sensor of the container C contained in the upright refrigerator 900 and the image sensor 800 mounted to the refrigerator 900. FIGS. 31 and 32 are diagrams illustrating a gas sensor and an image sensor mounted to a storage chamber divided by an internal shelf of the upright refrigerator according to an embodiment of the disclosure. If the container C including the gas sensors (100, 300) as shown in FIGS. 18 to 20 is accommodated in the storage chamber 903 as shown in FIG. 29, the image sensor 800 is installed at the inside of the refrigerator cover 901 in such a manner that the image sensor 800 can obtain the images of the gas sensors (100, 300) when the refrigerator cover 901 is closed.

If the container C including the gas sensor 100 as shown in FIGS. 16 and 17 is accommodated in the storage chamber 903 as shown in FIG. 30, the image sensor 800 is installed at the bottom of the refrigerator shelf facing the gas sensor 100.

In addition, as shown in FIG. 31, the gas sensor 100 may be installed at the wall of the storage space divided by a shelf. The image sensor 800 for obtaining the image of the gas sensor 100 is installed at the inside of the wall to face the gas sensor 100 as shown in FIG. 32, so that the image sensor 800 reacts with the target gas and thus obtains the image of the discolored gas sensor 100. The installation position or the number of gas sensors 100 shown in FIGS. 31 and 32 are merely exemplary, and other installation positions or other numbers of gas sensors 100 may be applied to the refrigerator 900 in such a manner that the gas sensors may be installed at the wall of the refrigerator 900.

If the target food stored on a specific shelf becomes rotten, the gas sensor 100 detects the gas generated in the rotting process of food, so that the image of the discolored gas sensor 100 can be obtained from the image sensor 800. The controller of the refrigerator 900 may determine whether the target food is rotten on the basis of the gas-sensor discoloration information shown in the image obtained from the image sensor 800, and may determine the position of the image sensor 800 having transmitted the image of the discolored gas sensor 100 to be the position of rotten food. The refrigerator 900 may display the position of the rotten food through the display unit in such a manner that the user can recognize the rotten state of food.

If the image sensor 800 mounted to the refrigerator 900 obtains the image of the gas sensor 100, the refrigerator 900 may calculate the color change of the gas sensor 100 on the basis of the above image, and may determine a food state. Various embodiments for determining a state of the food state (O) (i.e., a state of kimchi) by detecting color change of the gas sensor 100 will hereinafter be described in detail.

Figure 33:
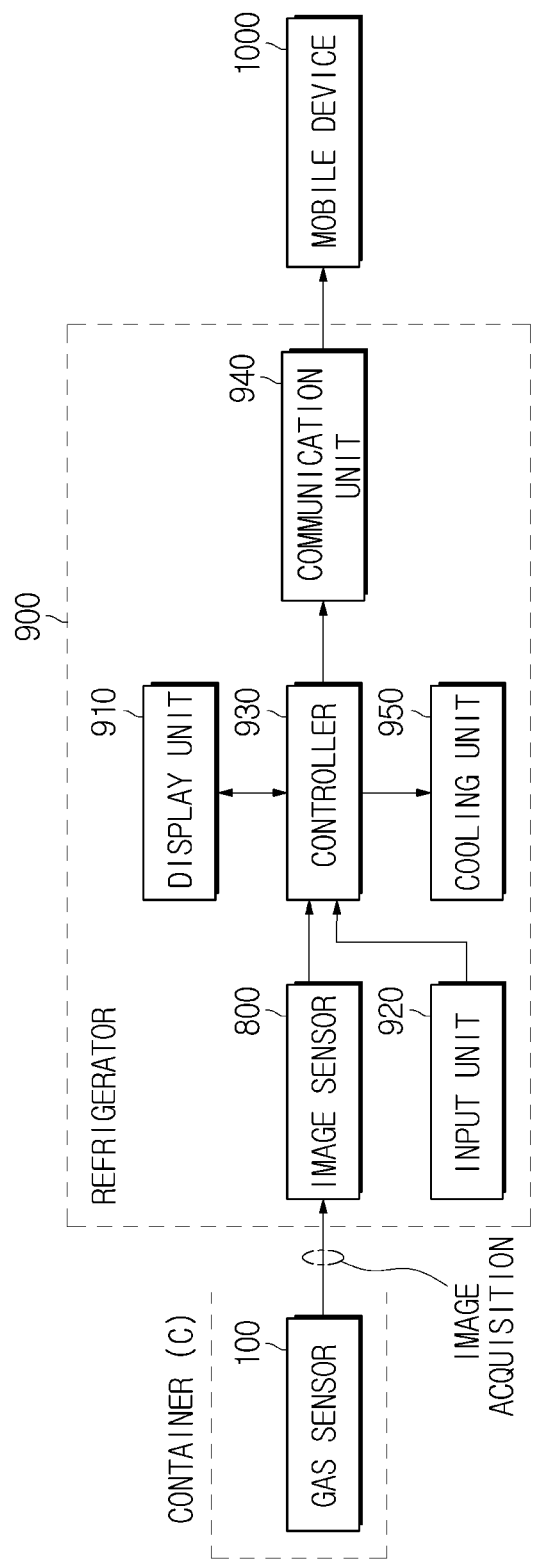
FIG. 33 is a block diagram illustrating a refrigerator according to an embodiment of the disclosure.

FIG. 33 is a block diagram illustrating a refrigerator 900 according to an embodiment of the disclosure.

Referring to FIG. 33, the refrigerator 900 may include an image sensor for obtaining an image of the gas sensor 100 mounted to the container C; a controller 930 for determining a state of the target food O using the image obtained from the image sensor 800; a display unit 910 for displaying information regarding the target food (O) state decided by the controller 930; a cooling unit 950 for adjusting a temperature of the storage chamber 903 by applying cool air to the storage chamber 903 according to the target food state decided by the controller 930; an input unit 920 for enabling a user to input commands related to operations of the refrigerator 900; and a communication unit 940 for transmitting information regarding the target food state decided by the controller 930 to an external mobile device 1000.

The image sensor 800 is installed at the storage chamber 903 of the refrigerator 900 or the shelf or door of the refrigerator 900 as shown in FIGS. 27 to 30, so that the image sensor 800 obtains the image of the gas sensor 100 mounted to the container C. The image sensor 800 may be any one of a photodiode, a CMOS image sensor, and a CCD, for example. The image sensor 800 may obtain the image of the gas sensor 100 to detect the color change of the detection unit 120 contained in the gas sensor 100. The categories of the image sensor 800 are not limited to the above-mentioned examples, and the optical device capable of obtaining the image of the gas sensor 100 may be contained in the image sensor 800 of this embodiment. A plurality of containers C, each of which includes the gas sensor 100, may be accommodated in the storage chamber 903, and the image sensor 800 is installed at each space in which the container C can be located so that a plurality of image sensors 800 may also be installed as necessary.

The image sensor 800 may successively obtain the image of the gas sensor 100, may obtain data of the color change by sampling the obtained image, and may obtain the image of the gas sensor 100 at intervals of a predetermined time, so that the image sensor 800 may obtain the data regarding the color change. The image sensor 800 may be successively exposed to a low-temperature environment because it is installed in the refrigerator 900. Therefore, frost may accumulate on the image sensor 800, so that it may be impossible to obtain a clear image of the gas sensor 100. The image sensor 800 according to the disclosed embodiment may include a predetermined heating unit capable of melting frost, or may be formed of a material for preventing the occurrence of frost.

If the image sensor 800 obtains an image of the gas sensor 100 and transmits the obtained image to the controller 930, the controller 930 may calculate a difference in color between a pre-image obtained before the image sensor 800 is exposed to the target gas and a post image obtained after the image sensor 800 is exposed to the target gas. That is, the controller 930 may calculate a difference in color between a first color obtained before the image sensor 800 is exposed to target gas of the detection unit 120 constructing the gas sensor 100 and a second color obtained after the image sensor 800 is exposed to the target gas of the detection unit 120, so that the controller 930 may calculate the presence or absence of color change of the detection unit 120 and the degree of such color change. For example, after exposure to the initial color and the target gas of the detection unit 120, a color difference of the detection unit 120, shown in the images received from the image sensor 800, is calculated. In this case, the degree of discoloration can be recognized on the basis of a specific time before the sensor is exposed to the target gas. Alternatively, a color difference between the detection-unit (120) color shown in a currently transmitted image and the other detection-unit (120) color shown in a previously transmitted image is continuously calculated. In this case, it may be possible to recognize the degree of discoloration as time goes by. Although the color difference is calculated using any one of the above-mentioned schemes, it should be noted that desired data can be obtained through a predetermined operation.

The controller 930 compares the color difference with pre-stored data, and obtains information regarding the target food O.

The controller 930 configures the discoloration data of the detection unit 120 constructing the gas sensor 100 and data indicating a state of the target food O corresponding to the color change (discoloration) of the detection unit 120 in the form of a database (DB), so that the DB-formatted result can be pre-stored. The controller 930 compares the calculated color difference of the detection unit 120 with pre-stored data, and thus determines a state of the target food O.

If the user detects the color change of the gas sensor 100 using the image sensor and uses the DB information, instead of observing the color change of the gas sensor 100 with the naked eye, a food state can be more accurately determined.

If a state of the target food O is determined, the controller 930 may display a state of the target food O determined through the display unit 910. For example, if the target food O is kimchi and the kimchi is raw kimchi, the controller 930 may display a kimchi state indicating raw kimchi on the display unit 910.

If the user inputs a desired command for displaying such information, the controller 930 may display information regarding the food state on the display unit 910. For example, if the user selects the container C to be confirmed through the input unit 920, the controller 930 may display the target food (O) state calculated from the images received from the image sensor 800 configured to detect the gas sensor 100 of the selected container on the display unit 910. If the target food O stored in the selected container C is kimchi and this kimchi is raw kimchi, the controller 930 may display specific information on the display unit 910, the specific information indicating that kimchi is stored in the corresponding container C and this kimchi is raw kimchi. The input unit 920 may have a user interface through which the user can intuitively select the container C.

The user may confirm information displayed on the display unit 910, and may input a command for a desired state of the target food O through the input unit 920. The controller 930 may receive a command regarding the target food O from the user through the input unit 920, so that the controller 930 may control a temperature of the storage chamber 903. For example, if the user inputs a command for maintaining a current kimchi state through the input unit 920, the controller 930 may determine a temperature (capable of maintaining a current kimchi state) of the storage chamber 903 in consideration of a current kimchi state, and adjust a temperature of the storage chamber 903 by transmitting a control signal to the cooling unit 950. Alternatively, if the user inputs a desired command for kimchi ripening through the input unit 920, the controller 930 may determine a temperature of the storage chamber 903 in consideration of a current kimchi state to perform additional ripening of the kimchi, may transmit a control signal corresponding to the determined temperature to the cooling unit 950, and may thus adjust a temperature of the storage chamber 903.

Alternatively, the controller 930 may determine a temperature of the storage chamber 903 in such a manner that the target food O reaches an optimum ripening state and the optimum ripening state can be maintained in response to the determined state of the target food O, may transmit a control signal corresponding to the determined temperature to the cooling unit 950, and may thus automatically adjust the temperature of the storage chamber 903.

If information regarding a user-desired storage state of the target food (O) is previously input, the controller 930 may monitor the color change of the gas sensor 100 and may automatically control a temperature of the storage chamber 903 in response to the state of the target food O, so that the target food O reaches a desired storage state and this desired storage state can be maintained.

In addition, the refrigerator 900 according to an embodiment may include a communication unit 940 capable of communicating with the external mobile device 1000, so that image data of the gas sensor 100, obtained from the image sensor 800, may be transmitted to the mobile device 1000. Alternatively, information related to the target food O, obtained from the gas sensor 100, may also be transmitted to the mobile device 1000. The mobile device 1000 may include a device that is capable of communicating with the refrigerator 900. For example, the mobile device 100 may include a smartphone, a tablet PC, or the like. The mobile device 1000 may receive data received from the refrigerator 900, analyze the received data, and calculate information regarding the target food (O) state in the same manner as in the controller 930 of the refrigerator 900 so that the user can recognize the calculated information regarding the target food state. Alternatively, the controller 930 of the refrigerator 900 receives the calculated information regarding the target food (O) state, so that the user can recognize the received information.

The mobile device 1000 receives image data of the gas sensor 100, determines a state of the target food O on the basis of the received image data, displays the determined state for user recognition, receives a user-desired command, and has an application having a user interface through which a user-desired command is received and transmitted to the refrigerator 900. Communication between the mobile device 1000 and the refrigerator 900 may be short range wireless communication such as Wi-Fi or Bluetooth, or may be long range wireless communication. Therefore, the user may not directly confirm the display unit 910 of the refrigerator 900, and may frequently confirm a state of the refrigerator 900 through the mobile device 1000 indoors or outdoors.

Figure 34:
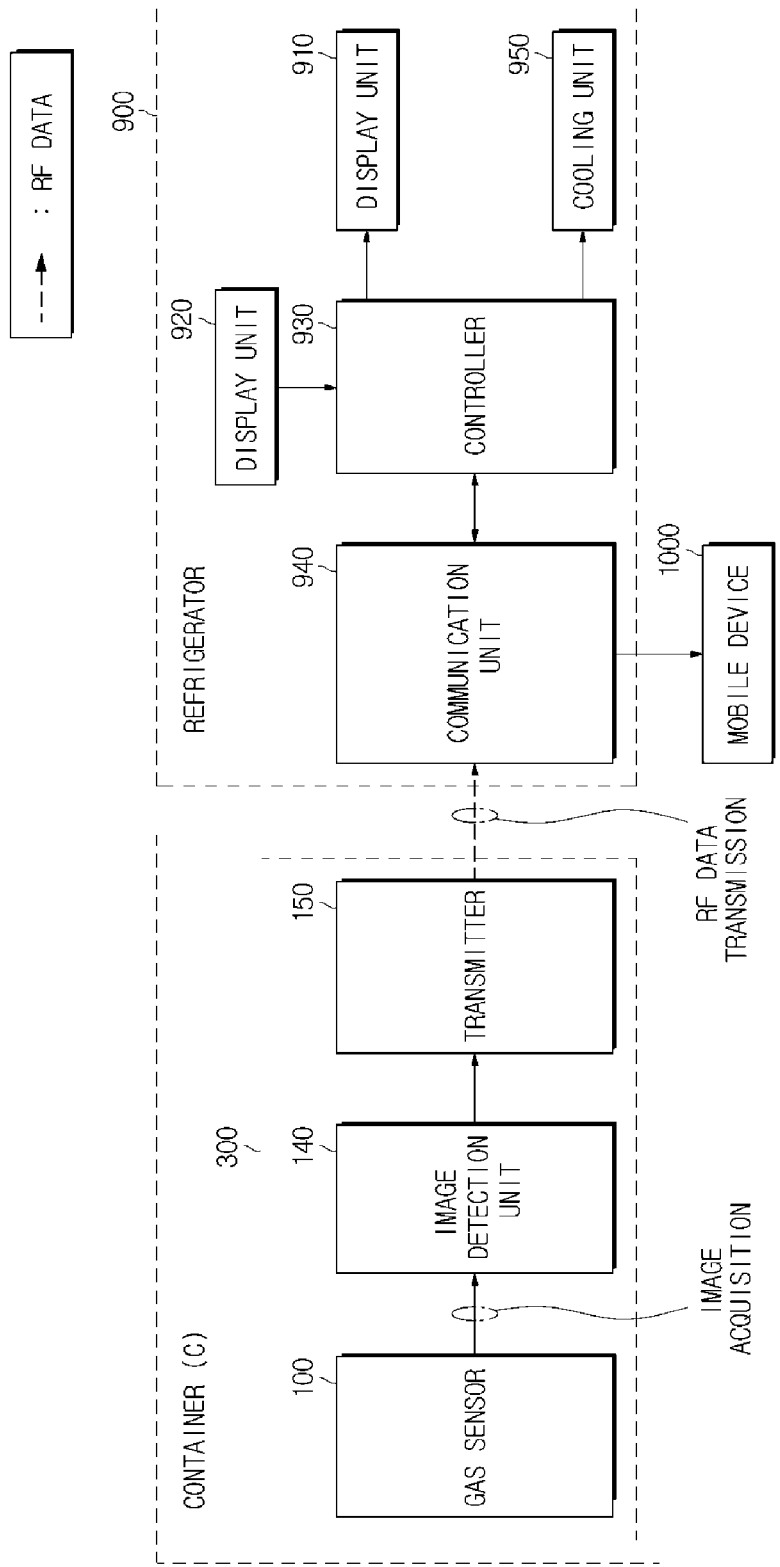
FIG. 34 is a block diagram illustrating a refrigerator according to an embodiment of the disclosure.

FIG. 34 is a block diagram illustrating a refrigerator 900 according to an embodiment of the disclosure.

Referring to FIG. 34, the refrigerator 900 may include a controller 930, a display unit 910, a cooling unit 950, an input unit 920, and a communication unit 940. The controller 930 may determine a state of the target food O using the gas sensor image received from the gas sensor 300 mounted to the container C. The display unit 910 may display information regarding the target food state decided by the controller 930. The cooling unit 950 may provide cool air to the storage chamber 903 according to the target food state determined by the controller 930, and may adjust a temperature of the storage chamber 903. The input unit 920 may enable the user to input a command related to the operation of the refrigerator 900. The communication unit 940 may transmit information regarding the target food state decided by the controller 930 to the external mobile device 1000.

The gas sensor 300 mounted to the container C is based on an embodiment of the disclosure. The gas sensor 300 according to an embodiment may include an image detection unit 140 for obtaining an image of the gas sensor 300.

Referring to FIG. 34, the gas sensor 300 according to an embodiment may include a gas sensor 100 of an embodiment shown in FIG. 5; an image detection unit 140 for obtaining an image of the color change of the gas sensor 100; a transmitter for transmitting image data of the gas sensor 100, obtained from the image detection unit 140, to the external device; and a battery 160 (not shown) for providing a power source to the image detection unit 140 and the transmitter 150.

The image detection unit 140 may use a photodiode, a CMOS image sensor, and a CCD. The image detection unit 140 may obtain images of the gas sensor 100 to detect color change of the detection unit 120 contained in the gas sensor 100. The image detection unit 140 may successively obtain the images of the gas sensor 100, and may obtain data regarding the color change by sampling the acquired images. Alternatively, the image detection unit 140 may obtain data of the color change by obtaining the image of the gas sensor 100 at intervals of a predetermined time.

The obtained data may be transmitted to the refrigerator 900 of an embodiment including the communication unit 940 through the transmitter 150. Various wireless communication schemes may be used for communication between the transmitter 150 of the gas sensor 300 and the communication unit 940 of the refrigerator 900.

If the communication unit 940 of the refrigerator 900 receives image data of the gas sensor 300 from the transmitter 150 of the gas sensor 300, the controller 930 of the refrigerator may calculate a color difference between a first image obtained before exposure to target gas and a second image after exposure to the target gas. That is, the controller 930 may calculate a color difference between a first color obtained before the detection unit 120 constructing the gas sensor 300 is exposed to the target gas and a second color obtained after the detection unit 120 constructing the gas sensor 300 is exposed to the target gas, such that the controller 930 can recognize the presence or absence of color change of the detection unit and can also recognize the degree of color change. For example, after the initial color of the detection unit 120 is shown and the detection unit 120 is then exposed to the target gas, the controller 930 may calculate a difference between colors of the detection unit 120 shown in the images transmitted from the gas sensor 300. In this case, the user can recognize the degree of color change on the basis of a specific time before exposure to the target gas. Alternatively, the controller 930 may continuously calculate a color difference between a color of the detection unit 120 shown in the image currently transmitted from the gas sensor 300 and a color of the detection unit 120 shown in the previously transmitted image. In this case, the user can recognize the degree of discoloration as time goes by. The controller 930 can obtain desired data through a predetermined operation, irrespective of the scheme for calculating such color difference.

The controller 930 may configure the discoloration data of the detection unit 120 constructing the gas sensor 300 and data indicating a state of the target food O corresponding to the color change (discoloration) of the detection unit 120 in the form of a database (DB), so that the DB-formatted result can be pre-stored. The controller 930 compares the calculated color difference of the detection unit 120 with pre-stored data, and thus determines a state of the target food O. The controller 930 may display a state of the target food O on the display unit 910 when the target food state is decided. For example, if the target food O is kimchi and this kimchi is raw kimchi, the controller 930 may display information indicating that a kimchi state is raw kimchi.

If the user inputs a desired command for displaying such information, the food state information is displayed on the display unit 910 in response to the input command. For example, if the user selects the container C to be confirmed through the input unit 920, the controller 930 may display a state of the target food O, obtained from the image received from the image detection unit 140 configured to obtain the image of the gas sensor 300 of the selected container C, on the display unit 910. If the target food O stored in the selected container C is kimchi and this kimchi is raw kimchi, the controller 930 may display specific information indicating that kimchi is stored in the corresponding container C and this kimchi is raw kimchi. The input unit 920 may have a user interface through which the user can intuitively select the container C. The display unit 190 may also have a user interface through which the user can intuitively recognize the state of the target food O.

The user may confirm information displayed on the display unit 910, and may input a command for a desired state of the target food O through the input unit 920. The controller 930 may receive a command regarding a desired state of the target food O through the input unit 920, so that it may control a temperature of the storage chamber 903. For example, if the user inputs a desired command for maintaining a current kimchi state through the input unit 920, the controller 930 may decide a temperature of the storage chamber 903 in such a manner that the kimchi state can be maintained in consideration of a current kimchi state, and may transmit a control signal to the cooling unit 950 to adjust a temperature of the storage chamber 903. Alternatively, if the user inputs a desired command for ripening the kimchi through the input unit 920, the controller 930 may determine a temperature of the storage chamber 903 in consideration of a current kimchi state so that the kimchi can be further ripened at the determined temperature. The controller 930 transmits a control signal corresponding to the determined temperature to the cooling unit 950, and adjusts a temperature of the storage chamber 903.

Alternatively, the controller 930 may determine a temperature of the storage chamber 903 in response to the determined target food state in such a manner that the target food O reaches an optimum ripening state and the optimum ripening state can be maintained at the determined temperature. The controller 930 may transmit a control signal corresponding to the determined temperature to the cooling unit 950, so that it may automatically adjust the temperature of the storage chamber 903.

If information regarding a user-desired storage state of the target food O is previously input, the controller 930 may monitor the color change of the gas sensor 300 and may automatically control a temperature of the storage chamber 903 in response to the state of the target food O, so that the target food O reaches a desired storage state and this desired storage state can be maintained.

In addition, the refrigerator 900 according to an embodiment may immediately transmit image data of the gas sensor 300, received from the gas sensor 300, to the mobile device 1000, or may transmit target food-associated information from the image of the gas sensor 300 to the mobile device 1000. The mobile device 1000 may receive data received from the refrigerator 900, analyze the received data, and calculate information regarding the target food state in the same manner as in the controller 930, so that the user can recognize the calculated information. Alternatively, the controller 930 of the refrigerator 9090 may receive information regarding the pre-calculated target food state, and display the received information for user recognition.

Figure 35:
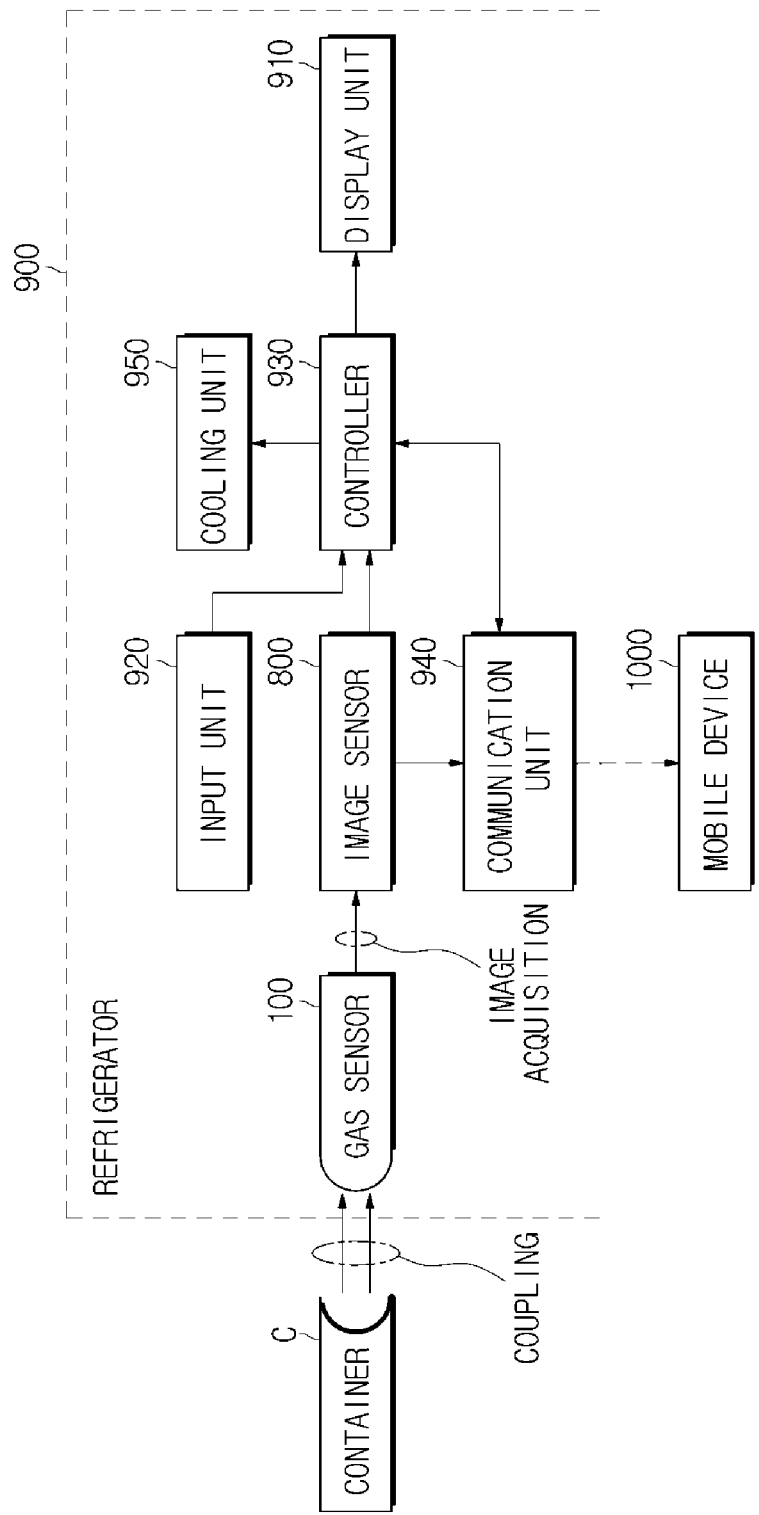
FIG. 35 is a block diagram illustrating a refrigerator according to an embodiment of the disclosure.
Figure 36:
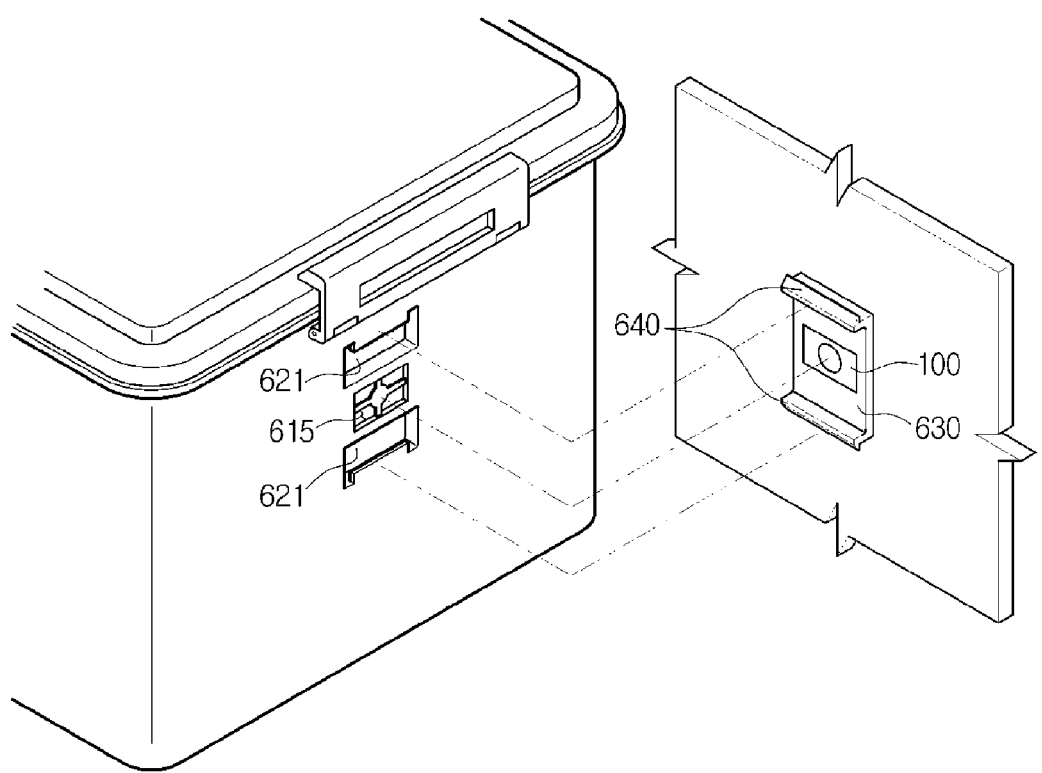
FIG. 36 illustrates a coupling structure between a gas sensor of a refrigerator and a container according to an embodiment of the disclosure.

FIG. 35 is a block diagram illustrating a refrigerator 900 according to an embodiment of the disclosure. FIG. 36 is a diagram illustrating a coupling structure between a gas sensor of the refrigerator 900 and a container C according to an embodiment of the disclosure.

Referring to FIG. 35, the refrigerator 900 may include a gas sensor 100, an image sensor 800, a controller 930, a display unit 910, a cooling unit 950, an input unit 920, and a communication unit 940. The gas sensor 100 is coupled to the container C contained in the storage chamber 903, so that it can detect the target gas generated from the target food O stored in the container C. The image sensor 800 may obtain an image of the gas sensor 100. The controller 930 may determine a state of the target food O using the images obtained from the image sensor 800. The display unit 910 may display information regarding the target food state decided by the controller 930. The cooling unit 950 may provide cool air to the storage chamber 903 in response to the target food state decided by the controller 930. The input unit 920 may enable the user to input commands associated with the operations of the refrigerator 900. The communication unit 940 may transmit information regarding the target food state decided by the controller 930 to the external mobile device 1000.

In accordance with an embodiment, the gas sensor 100 is not mounted to the container C and is stored in the storage chamber 903 of the refrigerator 900 including the container C. The gas sensor may obtain the correct detection result under the shielded environment. Therefore, as can be seen from FIG. 36, the gas sensor 100 along with a predetermined instrument unit to be coupled to the container C may be installed in the storage chamber 903. The container C may have a specific structure coupled to the instrument unit including the gas sensor 100. The instrument unit shown in FIG. 36 is similar in structure to the instrument unit 600 shown in FIGS. 18 to 20.

The instrument unit may include a main body 630 in which the gas sensor 100 is installed. A fixing unit 640 coupled to a fixing groove 621 formed at the wall of the container C is located at a lower part and an upper part of the main body, so that the instrument unit can be fixed to the wall of the container C when contacting the wall of the container C. The fixing unit 640 is fixed to couple the instrument unit to the container C. If the instrument unit is coupled to the container C, the scope or spirit of the disclosure is not limited to the shape, structure, position, and numbers shown in FIG. 26, and can also be applied to other shapes, other structures, other positions, and other numbers without change.

The gas sensor 100 may be separately mounted to the main body 630, or the gas sensor 100 along with the additional gas permeation layer may be mounted to the main body 630. A fixing groove 621 coupled to the fixing unit 640 of the instrument unit may be formed in the container C, and the fixing groove 621 may have a shape, structure, position, and number corresponding to the shape, structure, position, and number of the fixing units. When the gas sensor is coupled to the instrument unit, a hole 615 is formed at the wall of the container C so that the gas sensor can detect the target gas generated from the target food O stored in the container C. A gas permeation layer for transmitting only gas without transmitting liquid or solid may be installed so that the gas permeation layer can prevent the target food O accommodated in the container C from exiting the container C through the hole. When the container C is located in the storage chamber 903, the user may couple the container C to the above-mentioned instrument unit in such a manner that the hole 615 of the container C is coupled to the gas sensor 100 of the storage chamber 903.

The coupling structure shown in FIG. 36 is only exemplary, and the coupling structure between the gas sensor 100 and the container C is conceptually contained in the scope of the disclosure. Here, this gas sensor 100 is designed to detect the target gas generated from the container C.

Because the gas sensor 100 is coupled to the container C, the gas sensor 100 may detect the target gas. If the color change occurs, the image sensor 800 may obtain the image of the gas sensor 100.

The image sensor 800 may use a photodiode, a CMOS image sensor, and a CCD. The image sensor 800 may obtain an image of the gas sensor 100 to detect the color change of the detection unit 120 contained in the gas sensor 100. As many image sensors 800 as the number of gas sensors contained in the storage chamber 903 are provided, so that the image sensor can obtain the image of each gas sensor 100.

The image sensor 800 may successively obtain the image of the gas sensor 100, may obtain data of the color change by sampling the obtained image, and may obtain the image of the gas sensor 100 at intervals of a predetermined time, so that the image sensor 800 may obtain the data regarding the color change. If the image sensor 800 obtains the image of the gas sensor 100 and transmits the obtained image to the controller 930, the controller 930 may calculate a color difference between a first image obtained before exposure to the target gas and a second obtained after exposure to the target gas. That is, the controller 930 calculates a color difference between the first color obtained before exposure to target gas of the detection unit 120 constructing the gas sensor 100 and the second color obtained after exposure to target gas of the detection unit 120, so that the controller 930 may calculate the presence or absence of color change (discoloration) of the detection unit 120 and the degree of discoloration. For example, after exposure to the initial color and the target gas of the detection unit 120, a color difference of the detection unit 120, shown in the images received from the image sensor 800, is calculated. In this case, the degree of discoloration can be recognized on the basis of a specific time before the sensor is exposed to the target gas. Alternatively, a color difference between the detection unit (120) color shown in a currently transmitted image and the other detection-unit (120) color shown in a previously transmitted image is continuously calculated. In this case, it may be possible to recognize the degree of discoloration as time passes. Although the color difference is calculated using any one of the above-mentioned schemes, it should be noted that desired data can be obtained through a predetermined operation.

The controller 930 configures the discoloration data of the detection unit 120 constructing the gas sensor 100 and data indicating a state of the target food O corresponding to the color change (discoloration) of the detection unit 120 in the form of a database (DB), so that the DB-formatted result can be pre-stored. The controller 930 compares the calculated color difference of the detection unit 120 with pre-stored data, and thus determines a state of the target food O.

If a state of the target food O is determined, the controller 930 may display a state of the target food O determined through the display unit 910. For example, if the target food O is kimchi and the kimchi is raw kimchi, the controller 930 may display a kimchi state indicating raw kimchi on the display unit 910.

If the user inputs a desired command for displaying such information, the controller 930 may display information regarding the food state on the display unit 910. For example, if the user selects the container C to be confirmed through the input unit 920, the controller 930 may display the target food (O) state calculated from the images received from the image sensor 800 configured to detect the gas sensor 100 for detecting target gas of the selected container on the display unit 910. If the target food O stored in the selected container C is kimchi and this kimchi is raw kimchi, the controller 930 may display specific information on the display unit 910, the specific information indicating that kimchi is stored in the corresponding container C and this kimchi is raw kimchi. The input unit 920 may have a user interface through which the user can intuitively select the container C. The display unit 910 may also have a user interface through which the user can intuitively recognize the state of the target food O.

The user may confirm information displayed on the display unit 910, and may input a command for a desired state of the target food O through the input unit 920. The controller 930 may receive a command regarding the target food O from the user through the input unit 920, so that the controller 930 may control a temperature of the storage chamber 903. For example, if the user inputs a command for maintaining a current kimchi state through the input unit 920, the controller 930 may determine a temperature (capable of maintaining a current kimchi state) of the storage chamber 903 in consideration of a current kimchi state, and adjust a temperature of the storage chamber 903 by transmitting a control signal to the cooling unit 950. Alternatively, if the user inputs a desired command for kimchi ripening through the input unit 920, the controller 930 may determine a temperature of the storage chamber 903 in consideration of a current kimchi state to perform more ripening of the kimchi, may transmit a control signal corresponding to the determined temperature to the cooling unit 950, and may thus adjust a temperature of the storage chamber 903.

Alternatively, the controller 930 may determine a temperature of the storage chamber 903 in such a manner that the target food O reaches an optimum ripening state and the optimum ripening state can be maintained in response to the determined state of the target food O, may transmit a control signal corresponding to the determined temperature to the cooling unit 950, and may thus automatically adjust the temperature of the storage chamber 903. If information regarding a user-desired storage state of the target food (O) is previously input, the controller 930 may monitor the color change of the gas sensor 100 and may automatically control a temperature of the storage chamber 903 in response to the state of the target food O, so that the target food O reaches a desired storage state and this desired storage state can be maintained.

As shown in FIGS. 31 and 32, if the gas sensor is not coupled to the container, the gas sensor may detect the target gas generated from the target food stored in an installation region of the gas sensor. If the target food stored in a specific shelf becomes rotten, the gas sensor may detect the gas generated from the rotting process, so that the image of the discolored gas sensor can be obtained from the image sensor.

If the image sensor 800 obtains the image of the gas sensor 100 and transmits the obtained image to the controller 930, the controller 930 may calculate a color difference between a first image obtained before exposure to target gas and a second image obtained after exposure to the target gas. That is, the controller 930 may calculate a color difference between a first color obtained before exposure to the target gas of the detection unit 120 constructing the gas sensor 100 and a second color obtained after exposure to the target gas, so that the controller 930 may calculate the presence or absence of color change (discoloration) and the degree of such discoloration. The controller 930 configures the discoloration data of the detection unit 120 constructing the gas sensor 100 and data indicating a state of the target food O corresponding to the color change (discoloration) of the detection unit 120 in the form of a database (DB), so that the DB-formatted result can be pre-stored. The controller 930 compares the calculated color difference of the detection unit 120 with pre-stored data, and thus determines a state of the target food O. If a state of the target food (O) is a rotten state, the controller 930 may determine the position of the image sensor having transmitted the image indicating the rotten food state to be the position of rotten food. The installation position of each image sensor may be pre-stored, and the controller may decide the storage position of the rotten food on the basis of the pre-stored position information. The controller may display the position of rotten food on the display unit so that the user can recognize the rotten state of the food.

In addition, the refrigerator 900 according to an embodiment includes a communication unit 940 configured to communicate with the external mobile device 1000, and image data of the gas sensor 100, obtained from the image sensor 800, may also be transmitted to the mobile device 1000. Alternatively, information related to the target food O, obtained from the image of the gas sensor 100, may also be transmitted to the mobile device 1000. The mobile device 1000 receives data transmitted from the refrigerator 900, analyzes the received data, and calculates information regarding the state of the target food O, so that the user can recognize the calculated information. Alternatively, the controller 930 of the refrigerator 900 receives the previously calculated state information of the target food O, so that the user can recognize the received information. The mobile device 1000 receives image data of the gas sensor 100, determines the state of the target food O on the basis of the received image data, and displays the determined state for user recognition. The mobile device 1000 may have an application having a user interface through which a user-desired command is received and transmitted to the refrigerator 900. Communication between the mobile device 1000 and the refrigerator 900 may be short-distance wireless communication such as WiFi or Bluetooth, or may be long-distance wireless communication. Therefore, the user may not directly confirm the display unit 910 of the refrigerator 900, and may frequently confirm a state of the refrigerator 900 through the mobile device 1000 indoors or outdoors.

As is apparent from the above description, the gas sensor according to the embodiments can measure gas emitted from the ripening process of a target food (especially, kimchi), and can allow a user to visually recognize a discolored gas sensor, so that the user can intuitively recognize the ripening degree of target food (i.e., kimchi).

In addition, the refrigerator according to the embodiments measures a color change of the gas sensor using an image sensor, determines a state of target food on the basis of the measured color change, and displays the determined state on a display unit, so that the user can recognize the state of the target food.

The refrigerator according to the embodiment senses a color change of the gas sensor located in a storage chamber through an image sensor, determines the installation position of the discolored gas sensor, recognizes the position of rotten food, and displays the recognized position on a display unit for user recognition.

The above-described embodiments may be recorded in computer-readable media including program instructions to implement various operations embodied by a computer. The media may also include, alone or in combination with the program instructions, data files, data structures, and the like. The program instructions recorded on the media may be those specially designed and constructed for the purposes of embodiments, or they may be of the kind well-known and available to those having skill in the computer software arts. Examples of computer-readable media include magnetic media such as hard disks, floppy disks, and magnetic tape; optical media such as CD ROM disks and DVDs; magneto-optical media such as optical disks; and hardware devices that are specially configured to store and perform program instructions, such as read-only memory (ROM), random access memory (RAM), flash memory, and the like. The computer-readable media may also be a distributed network, so that the program instructions are stored and executed in a distributed fashion. The program instructions may be executed by one or more processors. The computer-readable media may also be embodied in at least one application specific integrated circuit (ASIC) or Field Programmable Gate Array (FPGA), which executes (processes like a processor) program instructions. Examples of program instructions include both machine code, such as produced by a compiler, and files containing higher level code that may be executed by the computer using an interpreter. The above-described devices may be configured to act as one or more software modules in order to perform the operations of the above-described embodiments, or vice versa.

Although a few embodiments of the disclosure have been shown and described, it would be appreciated by those skilled in the art that changes may be made in these embodiments without departing from the principles and spirit of the disclosure, the scope of which is defined in the claims and their equivalents.

What is claimed is:

1. A gas sensor fixable to a container configured to store a substance that may produce a target gas, the gas sensor comprising:
   a gas-permeable base;
   a detector provided on the base and configured to change color in response to a pH variation in the detector generated when the target gas, having permeated the gas-permeable base, reacts with the detector;
   an image detector configured to obtain an image of the detector;
   a heater configured to melt frost formed on at least one of the detector and the image detector, thereby maintaining the obtained image in a clear form; and
   a transmitter configured to output data regarding the image obtained from the image detector.

2. The gas sensor according to claim 1, wherein the detector includes a hydrophilic membrane having a detection solution.

3. The gas sensor according to claim 2, wherein the detection solution includes at least one pH indicator that changes color in response to pH variation generated when the detection solution reacts with the target gas.

4. The gas sensor according to claim 2, wherein:
   if acetic acid is contained in the target gas, the detection solution includes at least one of a bromothymol blue pH indicator from 0.001 weight percent to 0.1 weight percent and a chlorophenol red pH indicator from 0.001 weight percent to 0.1 weight percent.

5. The gas sensor according to claim 2, wherein the detection solution includes a buffer solution having a dissociation constant (pKa) of 3 to 10.

6. The gas sensor according to claim 5, wherein the buffer solution includes at least one of sodium acetate, sodium carbonate, sodium bicarbonate, and sodium citrate.

7. The gas sensor according to claim 6, wherein the sodium acetate buffer solution includes acetate ions of 0.1 mM to 1000 mM.

8. The gas sensor according to claim 5, wherein the detection solution includes a buffer solution in which conjugate ions having the same dissociation constant as in the target gas are dissolved.

9. The gas sensor according to claim 8, wherein a resolution of the gas sensor is changed according to the density of conjugate ions dissolved in the buffer solution.

10. The gas sensor according to claim 5, wherein:
    if the target gas is volatile organic acid, the detection solution includes a buffer solution having an initial pH value higher than a dissociation constant of target gas.

11. The gas sensor according to claim 10, wherein a sensing range of the target gas is changed according to the initial pH value of the buffer solution.

12. The gas sensor according to claim 2, wherein the detection solution includes at least one of glycerin, ethylene glycol, polyethylene glycol, and calcium chloride.

13. The gas sensor according to claim 2, wherein the detection solution is absorbed in the hydrophilic membrane and fixed thereto.

14. The gas sensor according to claim 2, wherein the hydrophilic membrane includes at least one of cellulose ester, glass fiber, cellulose acetate, cellulose fiber, litmus paper, Korean traditional paper, and filter paper.

15. The gas sensor according to claim 1, wherein the base includes a hydrophobic membrane.

16. The gas sensor according to claim 1, wherein the base includes at least one of polytetrafluoroethylene, thermoplastic polyurethane, polyethylene, low density polyethylene, linear low density polyethylene, high density polyethylene, and Tyvek.

17. The gas sensor according to claim 1, further comprising:
    a transparent membrane attached to the detector, and configured to prevent gas permeation.

18. The gas sensor according to claim 1, wherein the target gas includes gas generated from a ripening process of food.

19. The gas sensor according to claim 1, further comprising:
    a battery configured to provide a power source to the image detector and the transmitter.

20. The gas sensor according to claim 1, further comprising:
    a wireless power receiver configured to provide a power source to the image detector and the transmitter.

21. A refrigerator comprising:
    a container configured to store a substance that may produce a target gas;
    a gas sensor fixable to the container and including a gas-permeable base;
    a detector provided on the base and configured to change color in response to a pH variation in the detector generated when the target gas, having permeated the gas-permeable base, reacts with the detector;

an image sensor configured to obtain an image of the gas sensor; and a heater configured to melt frost formed on at least one of the detector and the image sensor, thereby maintaining the obtained image in a clear form.

22. The refrigerator according to claim 21, further comprising:

a controller configured to determine a state of a target food and a storage position of the target food on the basis of the gas sensor image obtained from the image sensor.

23. The refrigerator according to claim 22, wherein the controller is configured to pre-store data regarding the color of the gas sensor and the target food state based on the color.

24. The refrigerator according to claim 23, wherein the controller determines a color difference between a first color obtained before exposure to the target gas and a second color obtained after exposure to the target gas using the image obtained from the image sensor, and determines a state of the target food on the basis of the determined color difference using the pre-stored data.

25. The refrigerator according to claim 21, further comprising:

a display configured to display at least one of the target food state determined on the basis of the gas sensor image obtained from the image sensor and information regarding a storage position of the target food.

* * * * *